(12) United States Patent
Dutta

(10) Patent No.: US 10,973,456 B1
(45) Date of Patent: Apr. 13, 2021

(54) SYSTEM FOR SCREENING AND DIAGNOSIS OF SKIN CANCER

(71) Applicant: Banpil Photonics, inc., Santa Clara, CA (US)

(72) Inventor: Achyut Kumar Dutta, Sunnyvale, CA (US)

(73) Assignee: BANPIL PHOTONICS INC., Santa Clara, CA (US)

( * ) Notice: Subject to any disclaimer, the term of this patent is extended or adjusted under 35 U.S.C. 154(b) by 910 days.

(21) Appl. No.: 14/985,110

(22) Filed: Dec. 30, 2015

(51) Int. Cl.
*A61B 5/00* (2006.01)

(52) U.S. Cl.
CPC ............ *A61B 5/444* (2013.01); *A61B 5/0013* (2013.01); *A61B 5/0064* (2013.01); *A61B 5/0066* (2013.01); *A61B 5/0071* (2013.01); *A61B 5/742* (2013.01); *A61B 5/0059* (2013.01); *A61B 2560/0425* (2013.01); *A61B 2562/0233* (2013.01); *A61B 2562/04* (2013.01); *A61B 2562/222* (2013.01); *A61B 2562/223* (2013.01); *A61B 2576/02* (2013.01)

(58) Field of Classification Search
CPC ..... A61B 5/441; A61B 5/0071; A61B 5/0059; G06T 2207/30088
See application file for complete search history.

(56) References Cited

U.S. PATENT DOCUMENTS

| | | | | |
|---|---|---|---|---|
| 6,662,031 B1* | 12/2003 | Khalil | .................. | A61B 5/0059 600/310 |
| 8,509,880 B1* | 8/2013 | Zuluaga | .................... | A61B 1/00 600/472 |
| 2008/0194928 A1* | 8/2008 | Bandic | .................... | G16H 15/00 600/306 |
| 2010/0168586 A1* | 7/2010 | Hillman | ............. | G02B 23/2476 600/476 |
| 2010/0198026 A1* | 8/2010 | Young | .................. | A61B 5/0059 600/306 |
| 2011/0021908 A1* | 1/2011 | Lee | ....................... | A61B 5/0071 600/431 |
| 2015/0187068 A1* | 7/2015 | Krishna | ................ | G06F 19/321 382/128 |
| 2015/0238088 A1* | 8/2015 | Hufnagel | ........... | A61B 1/00055 600/476 |

* cited by examiner

*Primary Examiner* — Puya Agahi

(57) ABSTRACT

This invention provides a non-invasive diagnosis system that is not only capable of producing high-resolution, three-dimensional images of abnormalities of tissue growth inside the body but, it can also detect the type of abnormalities and their location using multispectral imaging techniques. It is possible to provide a portable, non-invasive device that is handheld and with which a person may use to screen themselves for early detection of skin cancer without the need to visit a physician. As the present invention uses broadband sources and/or multiple coherent sources, secondary factors such as oxygen metabolism or blood volume associated with the cancer tissues could also be detected to provide further verification of the type. This invention would raise the accuracy of diagnosis and reduce the rate of false positives and false negatives.

20 Claims, 44 Drawing Sheets

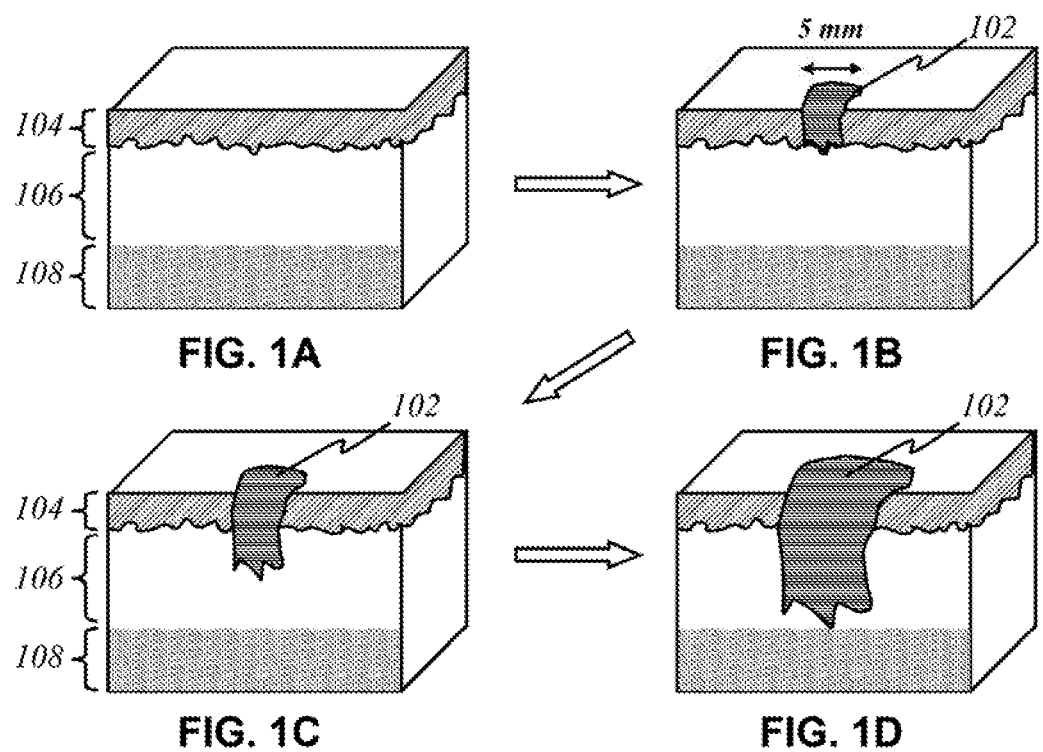
Stages of melanoma -- cross-section of lesion in skin

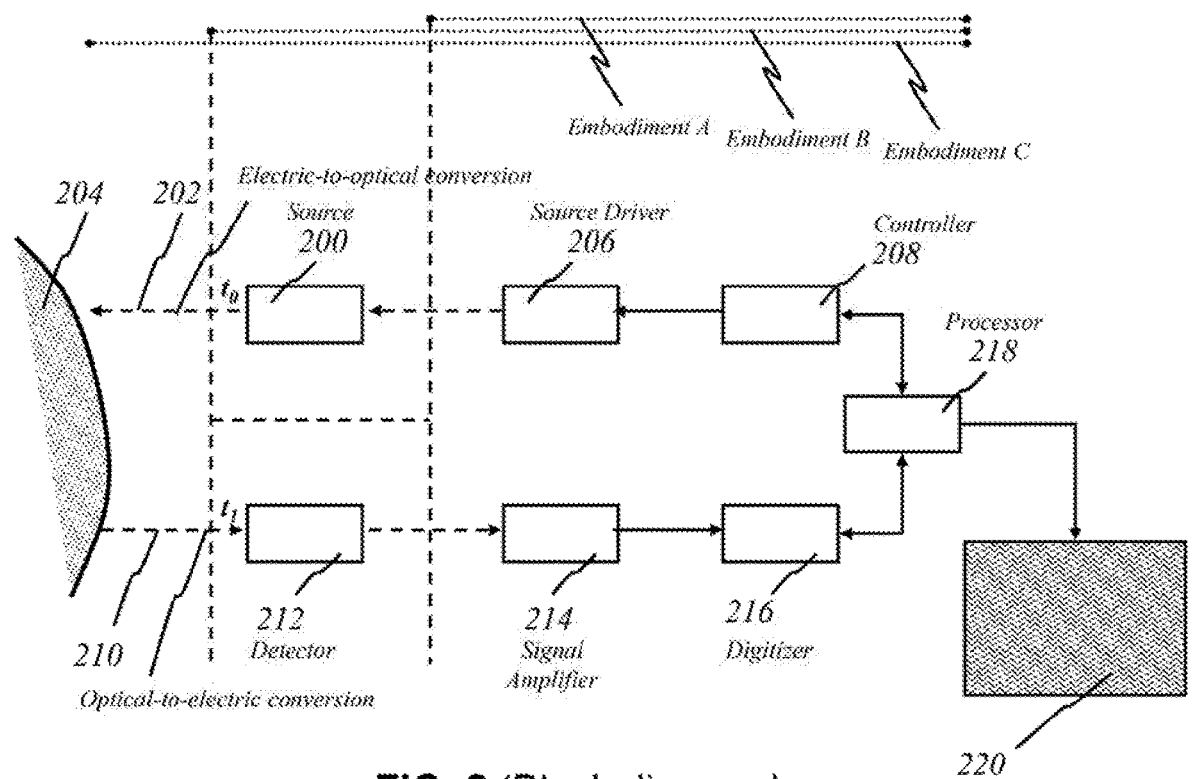
FIG. 2 (Block diagram)

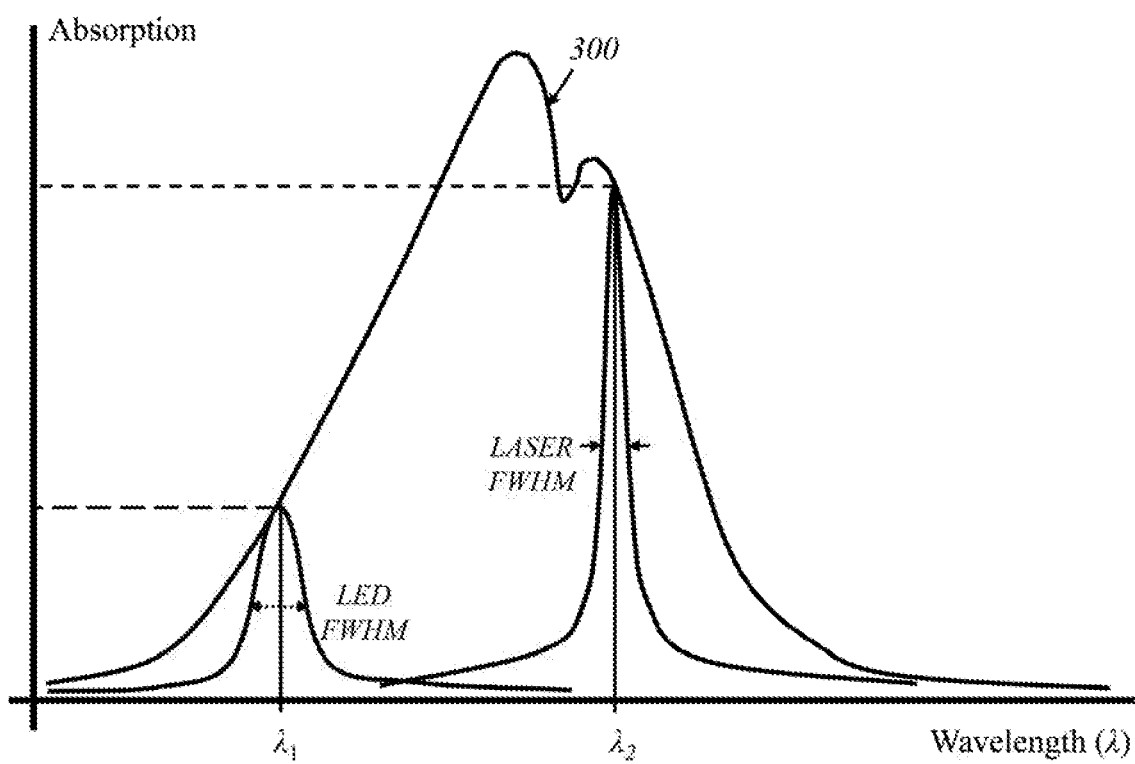
FIG. 3A sample absorption spectrum

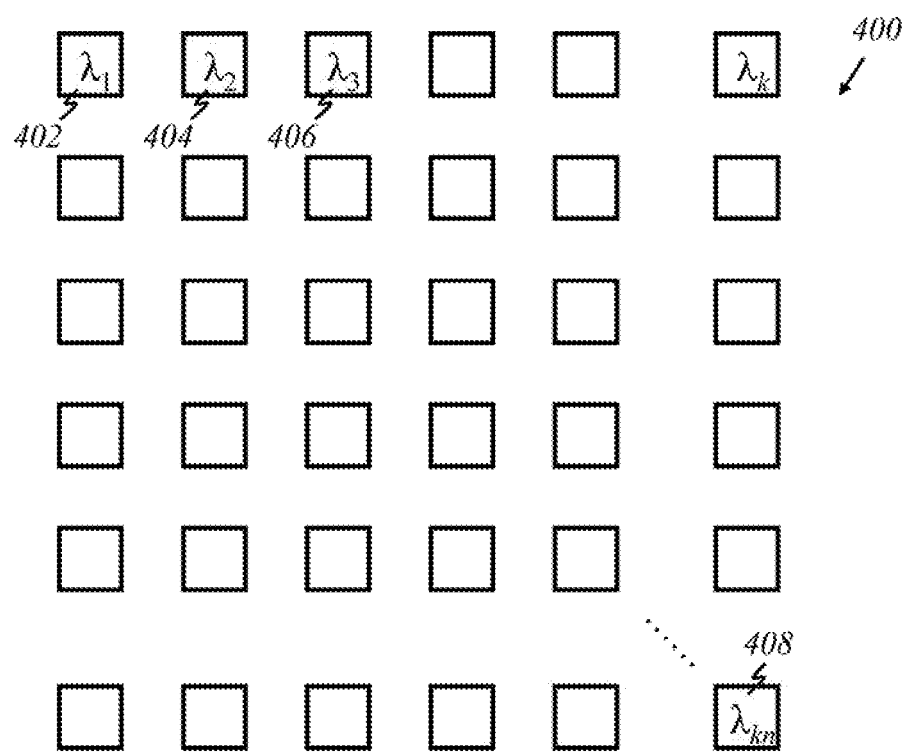
FIG. 4A Sources

Sources

Sources

Sources

Sources

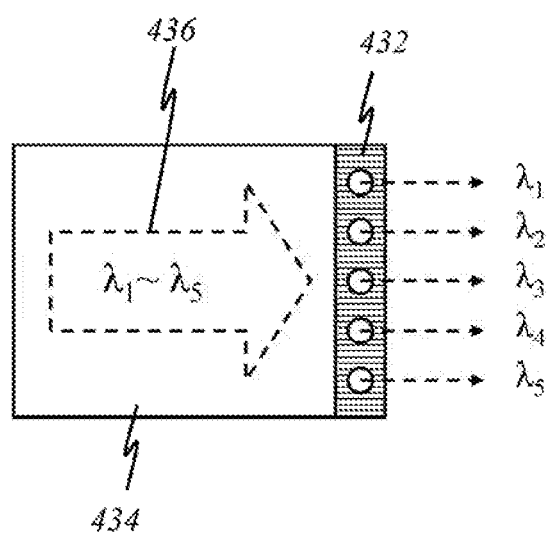
FIG. 4F Source w/ filter

Sources

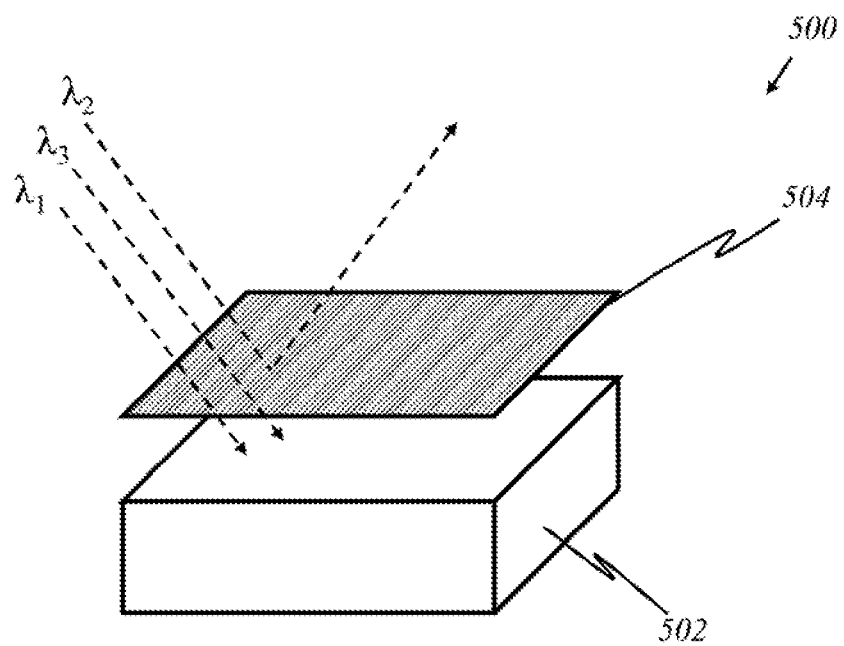
FIG. 5A Detector

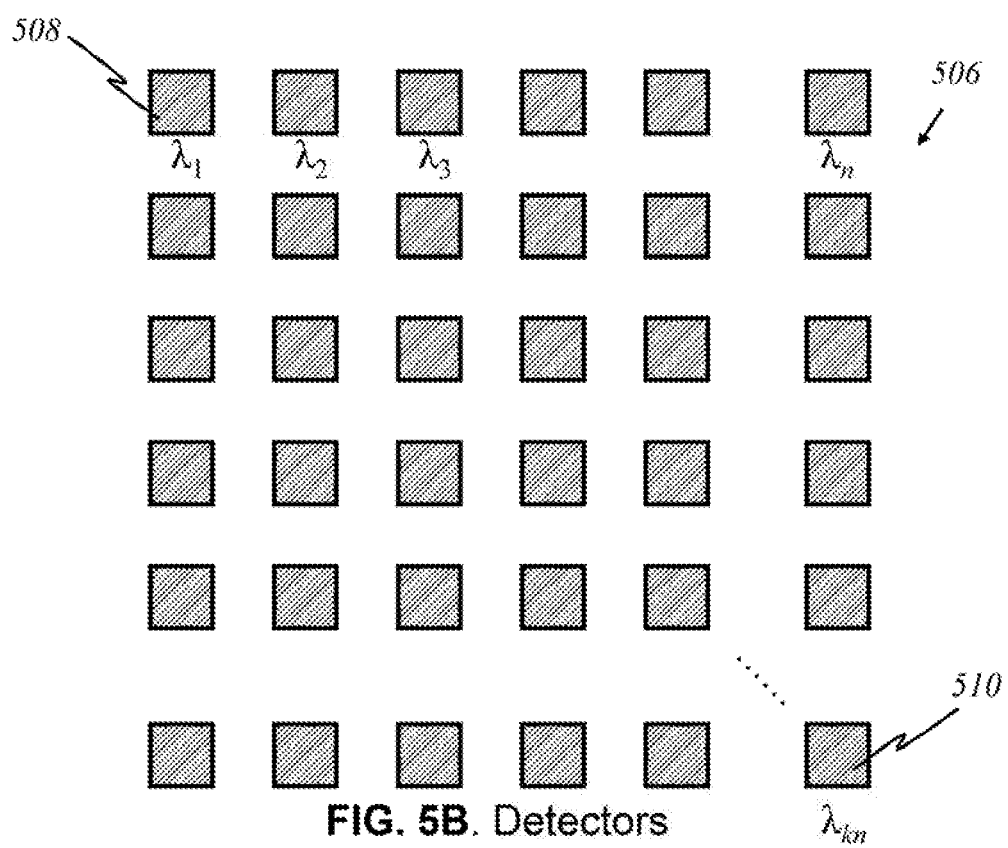
FIG. 5B. Detectors

Detectors

Source + detector

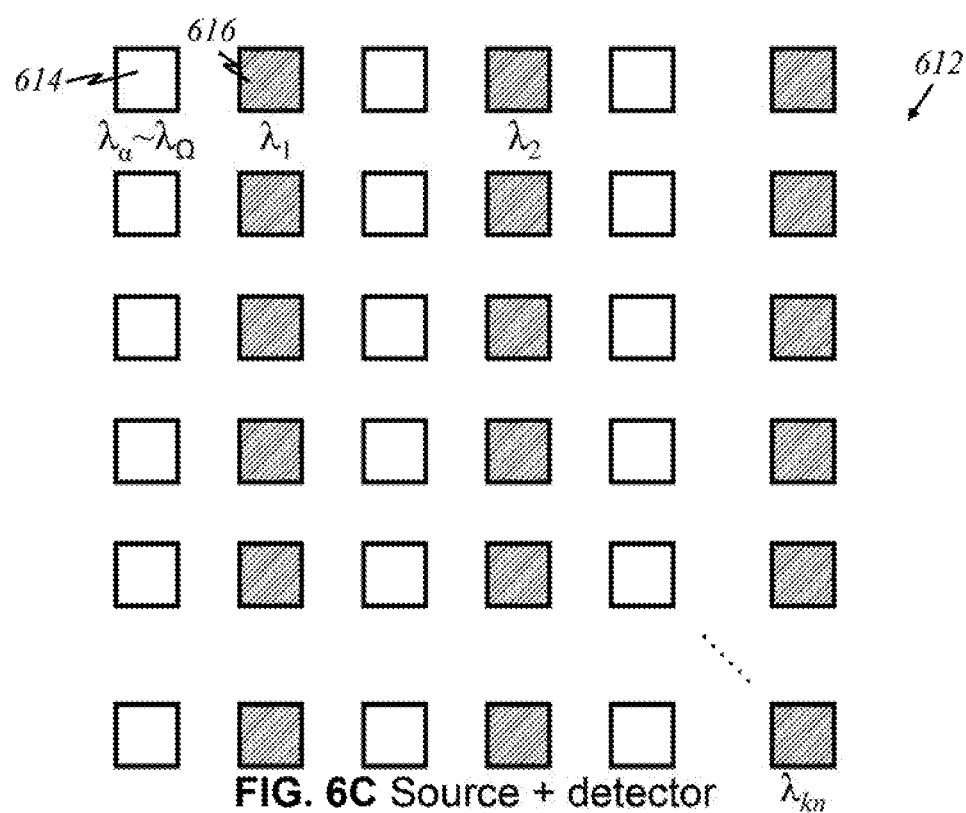
FIG. 6C Source + detector

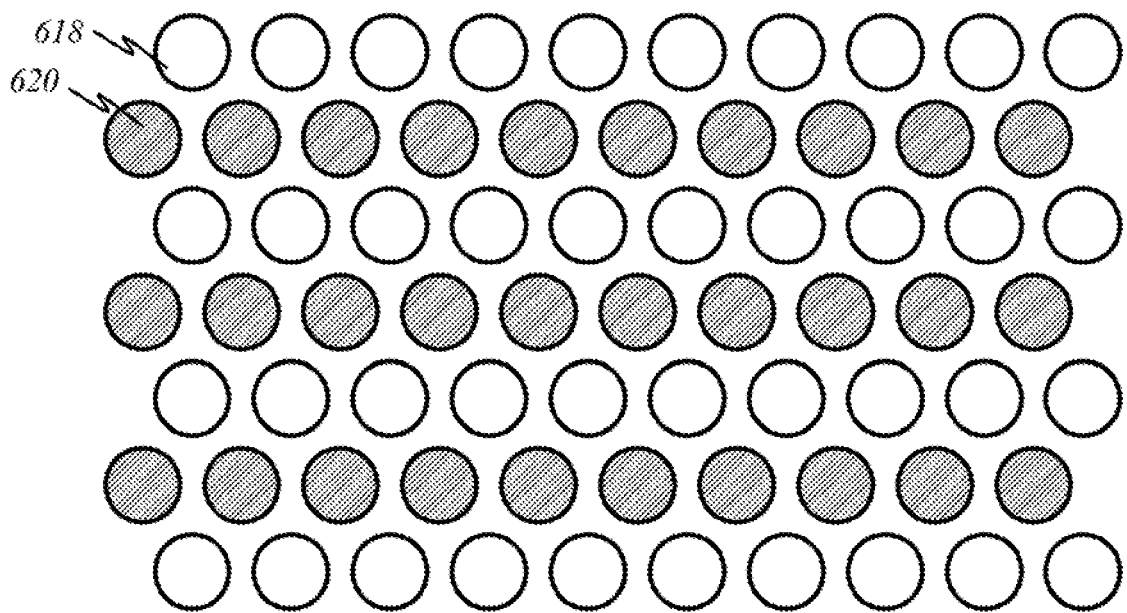
FIG. 6D Source + detector

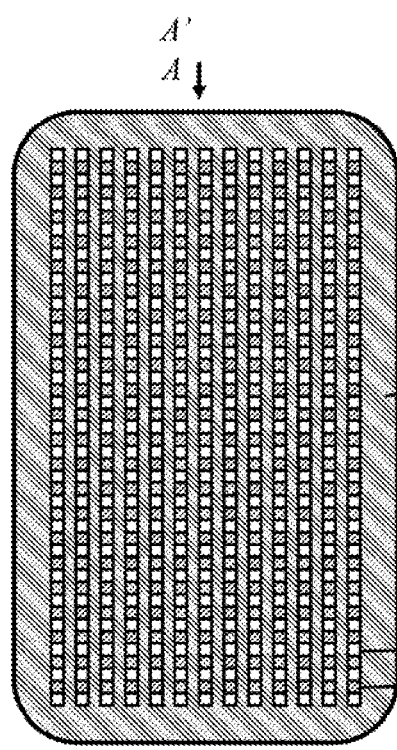
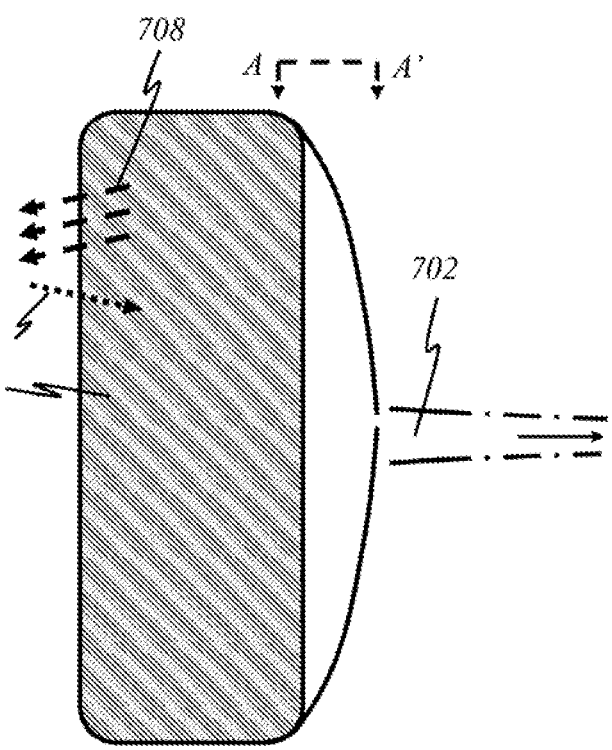
FIG. 7A  FIG. 7B
FIG. 7 Front & angled view of flat contact embodiment BEFORE

*Cross-sectional view of contact embodiment BEFORE contact*

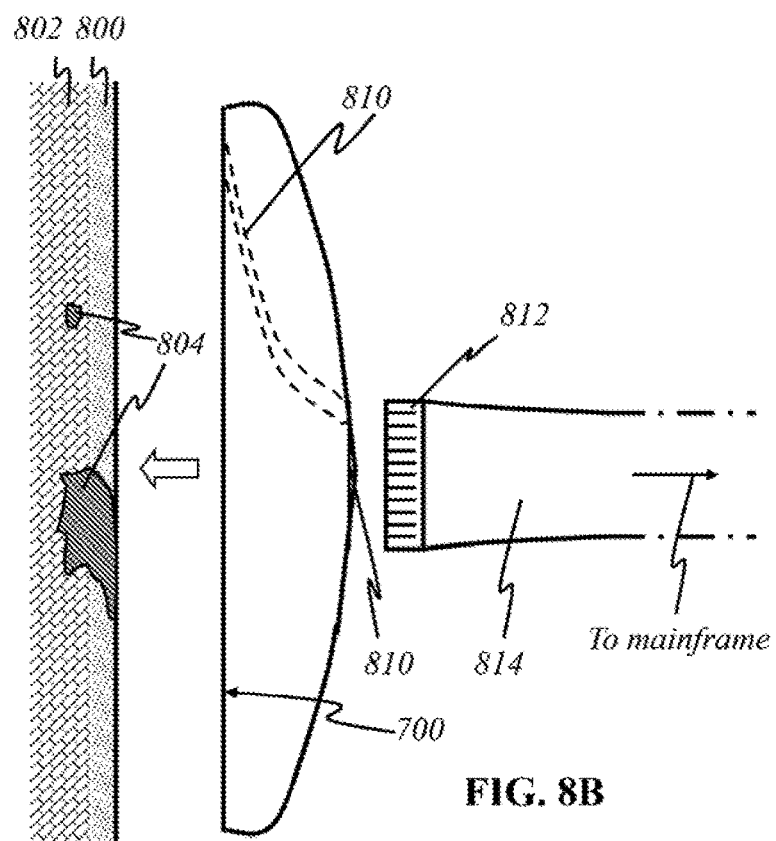
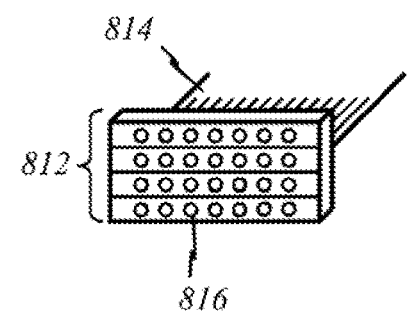
FIG. 8B  FIG. 8C
*Cross-sectional view of contact embodiment BEFORE contact (elec)*

*Cross-sectional view of contact embodiment (1) AFTER contact*

*Cross-sectional view of contact embodiment (2) AFTER contact*

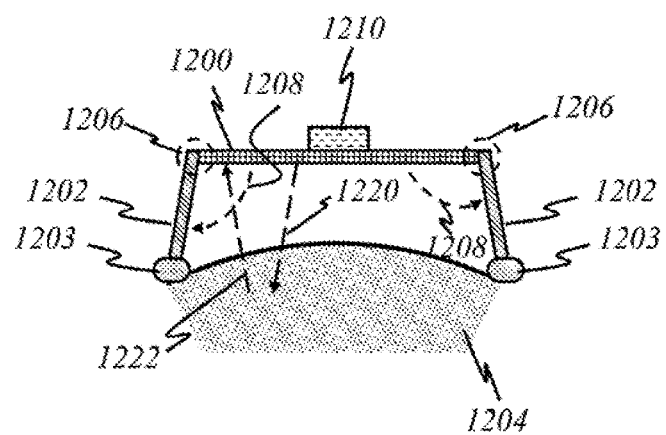
FIG. 12A Cross-sectional top view of non-contact, flip-open embodiment

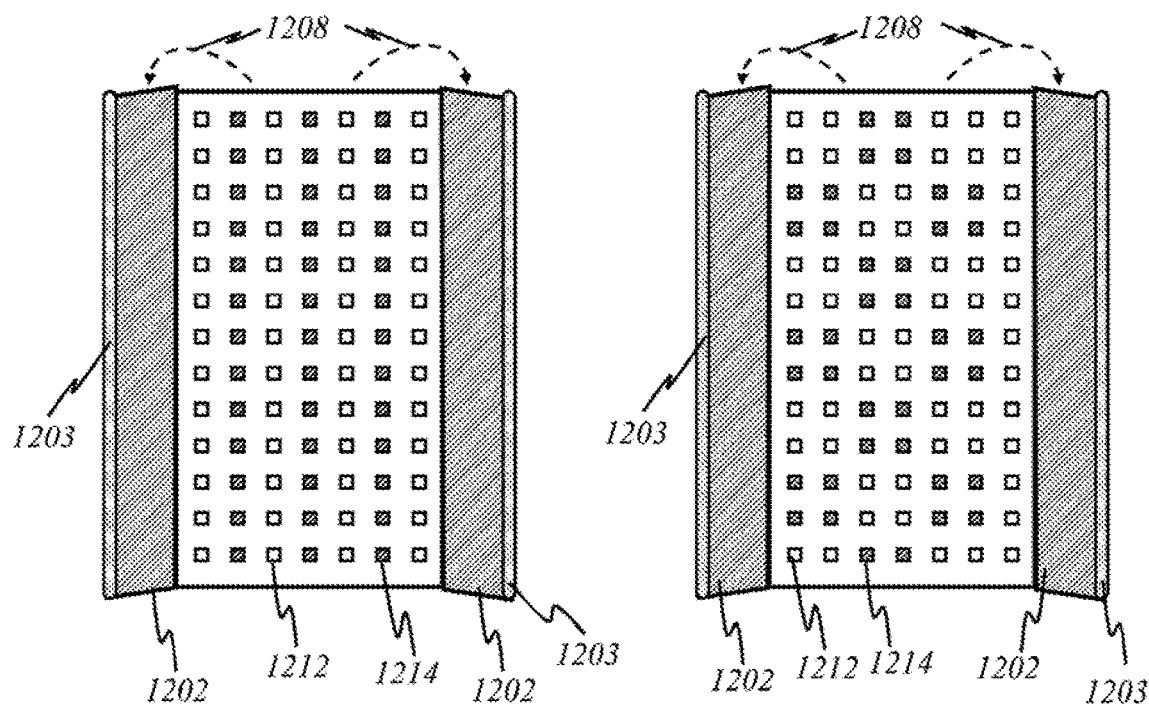
FIG. 12B  FIG. 12C
*Front view of flip-open embodiment (1)*

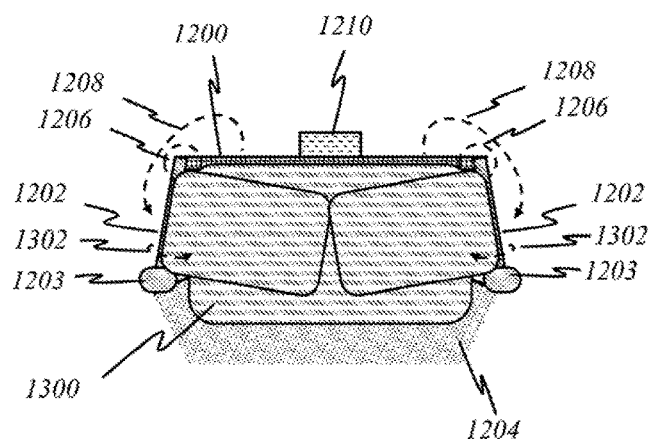
FIG. 13A Cross-sectional top view of non-contact, flip-open embodiment with shields

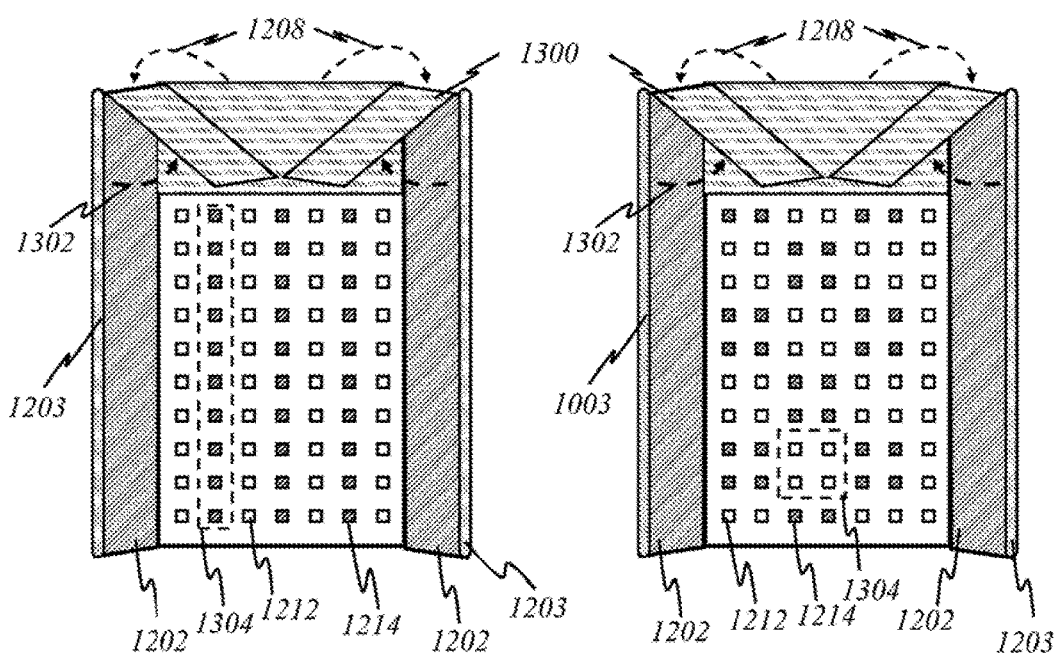
FIG. 13B  FIG. 13C
*Front view of flip-open embodiment (1) with shields*

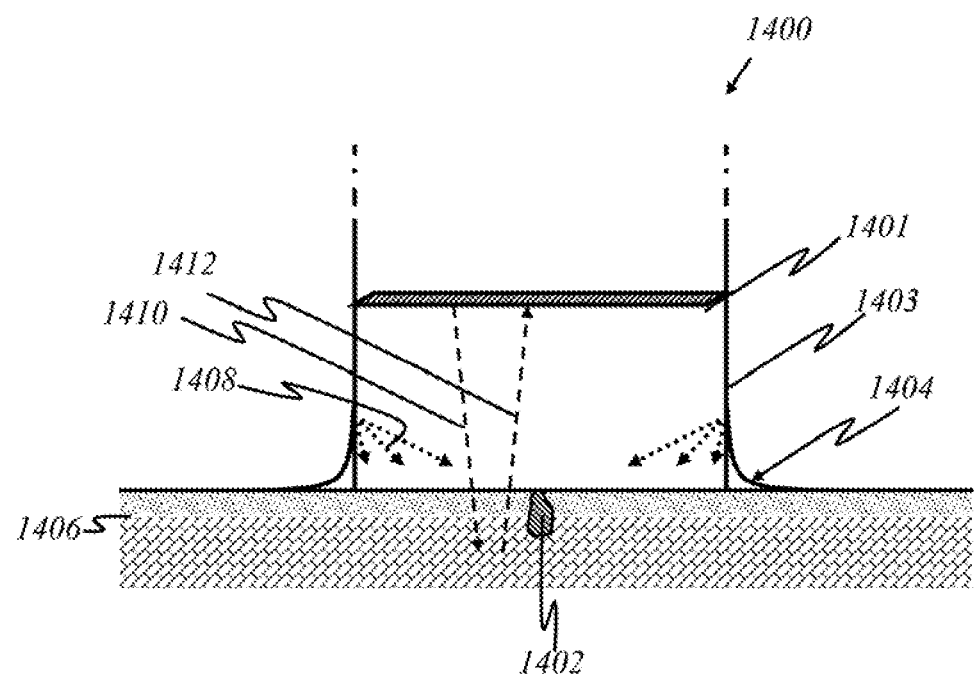
FIG. 14 Applying hot air

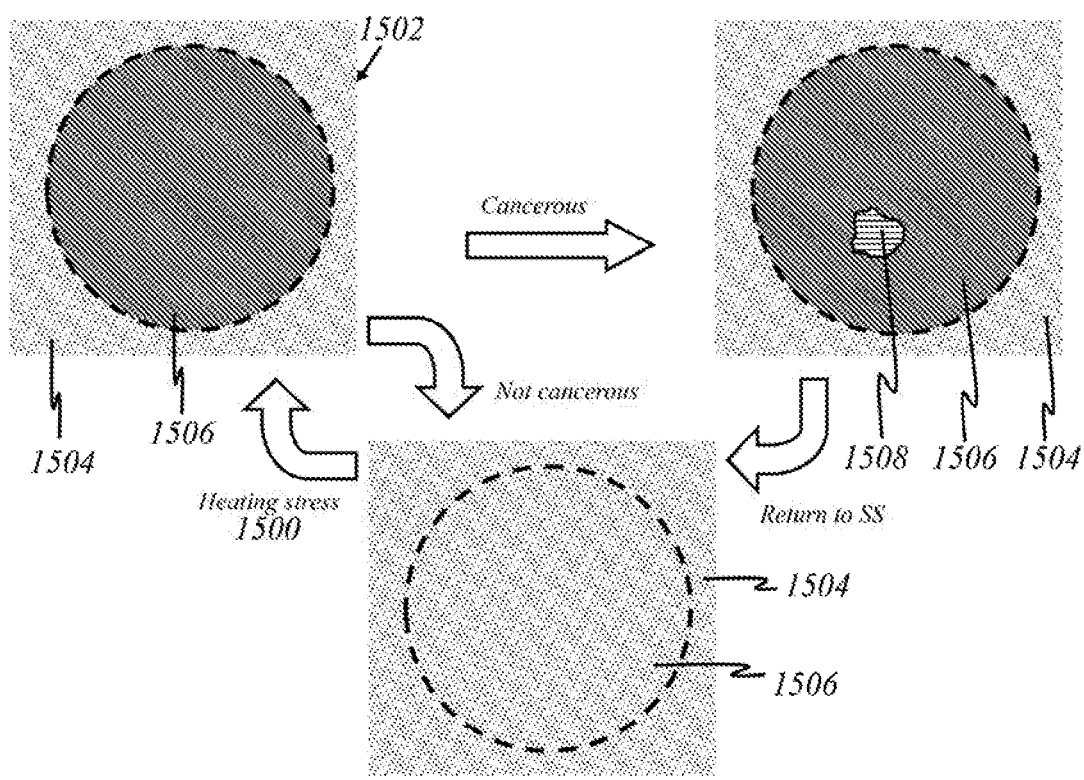
FIG. 15 Effect of hot air on skin with lesion

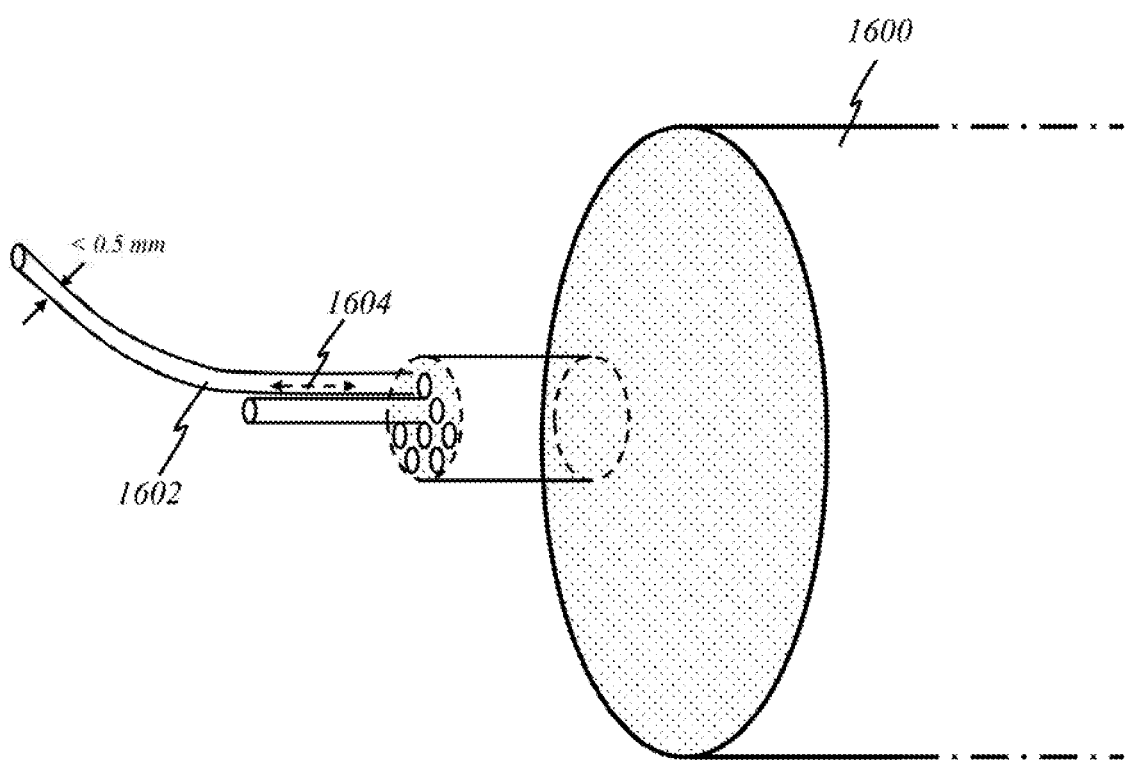
FIG. 16 Optical-fiber cable

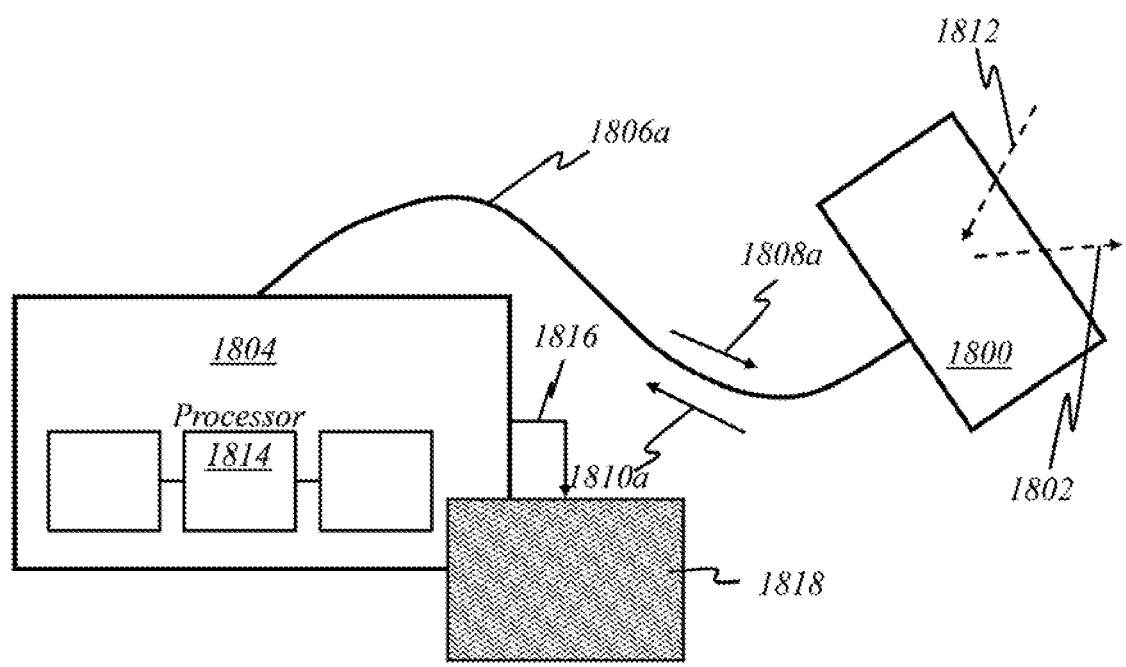
FIG. 18 Whole view (general schematic diagram)

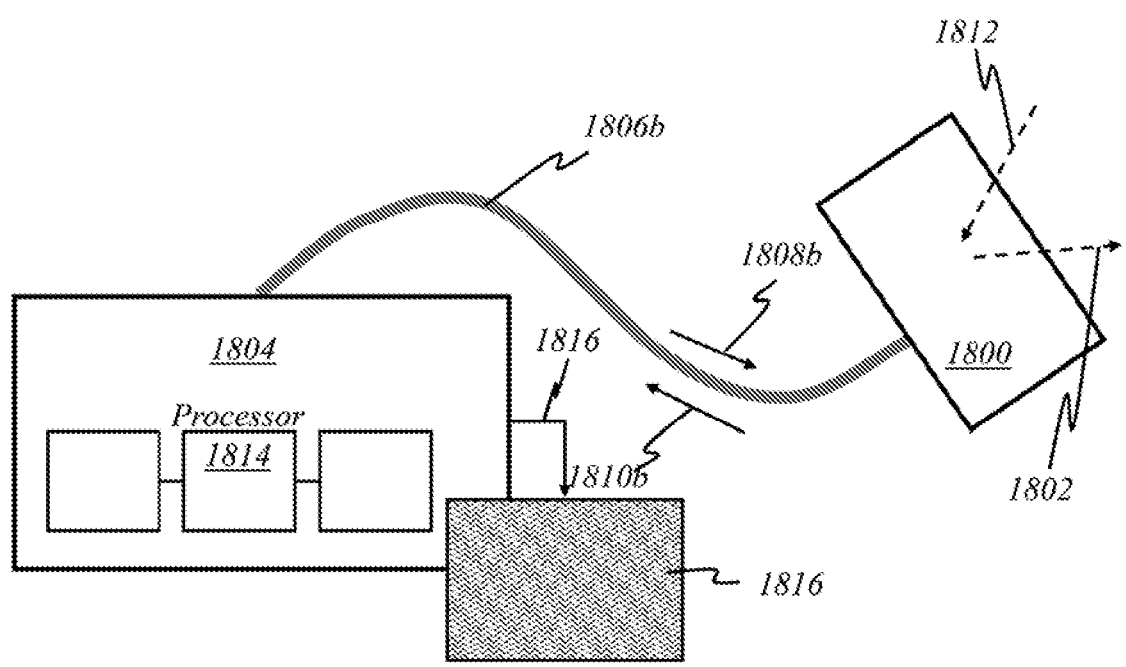
FIG. 19 Whole view (with electrical wire)

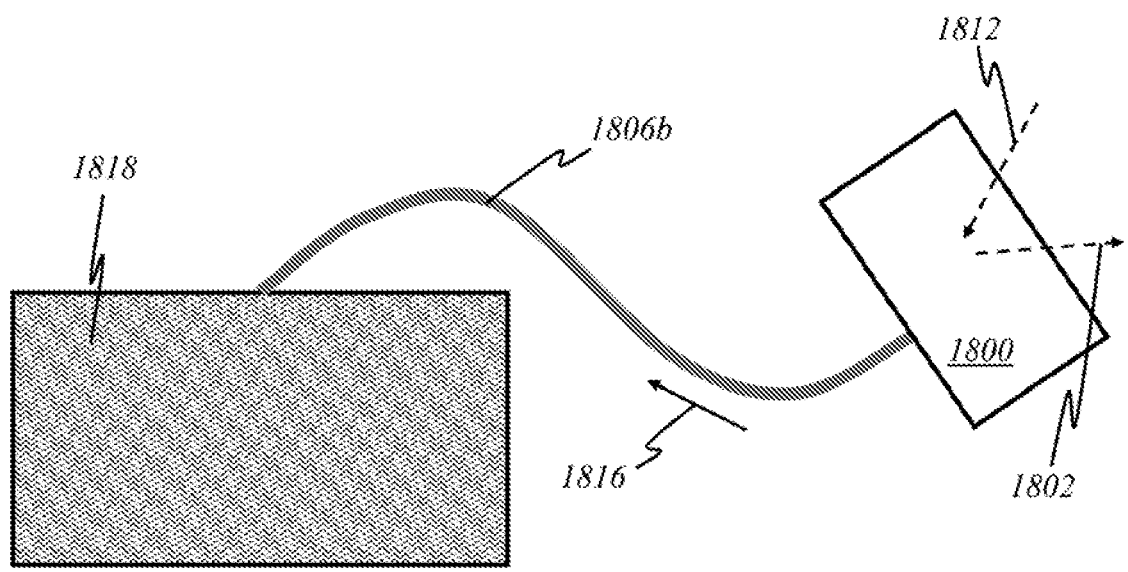
FIG. 20 Whole view (2) (with electrical wire)

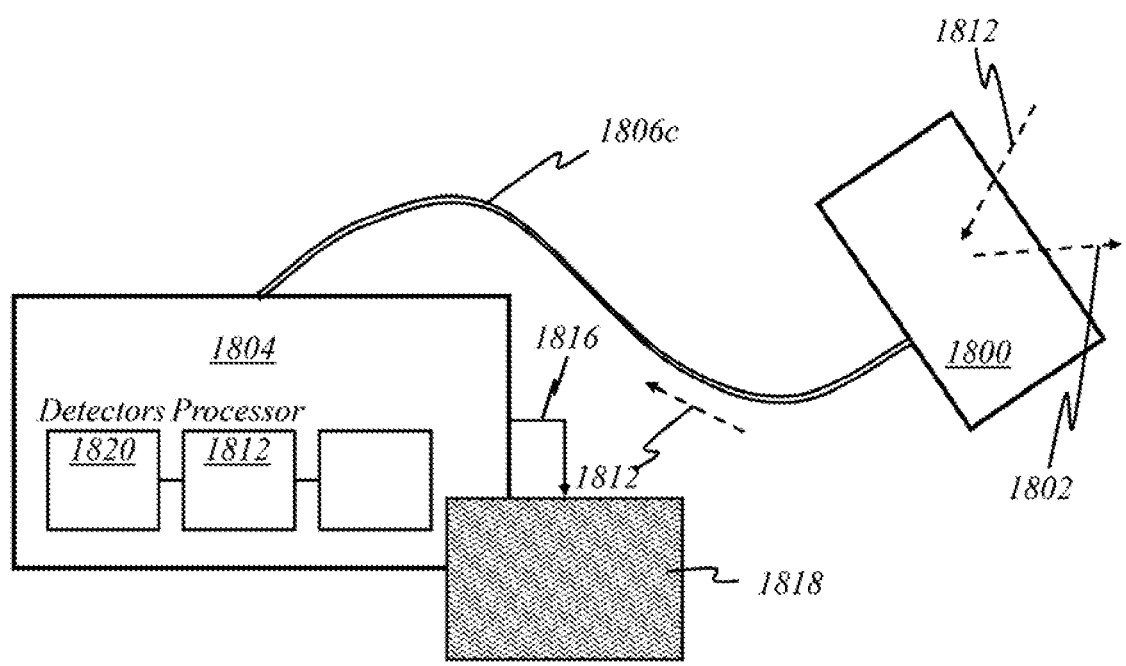
FIG. 21 Whole view (with optical fiber) (1)

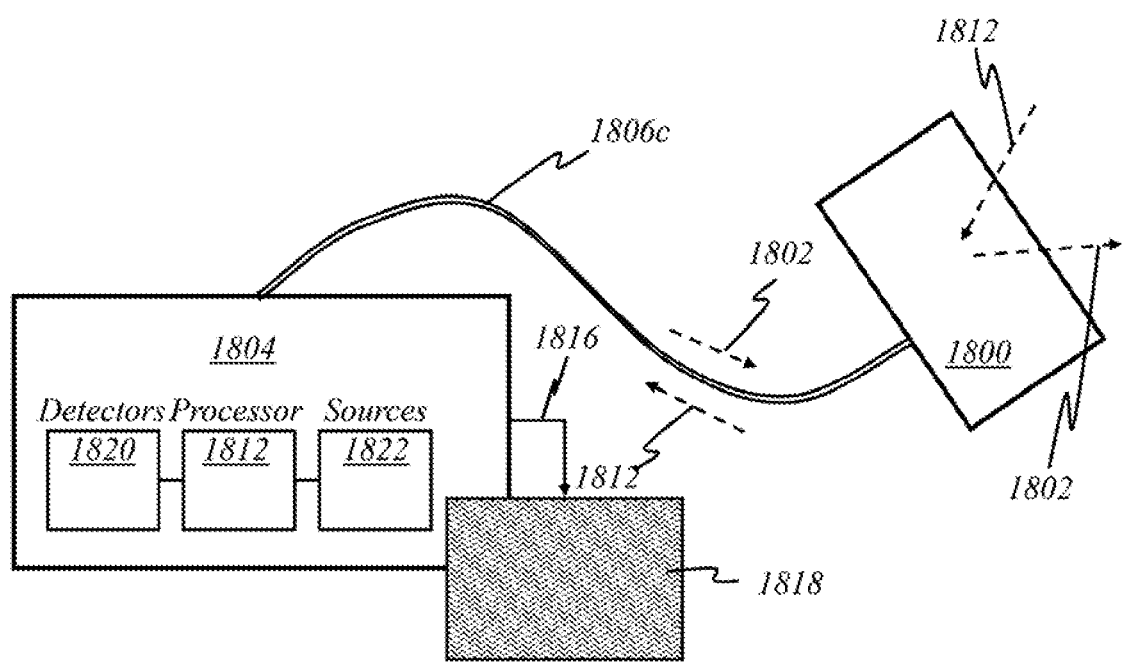
FIG. 22 Whole view (with optical fiber) (2)

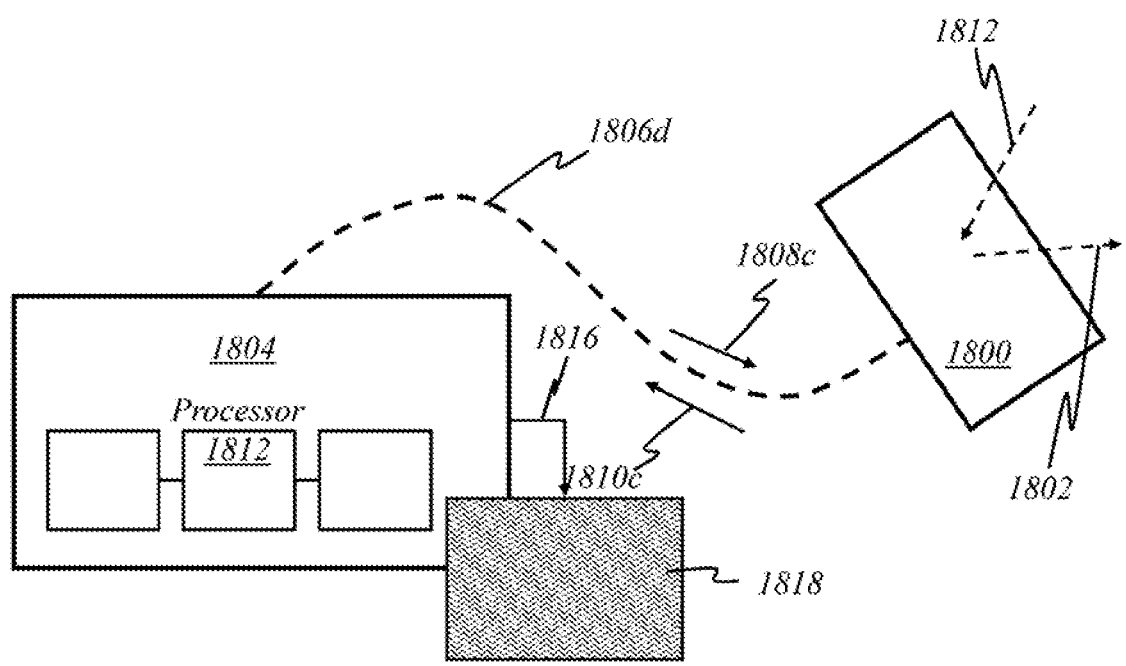
FIG. 23 Whole view (without wire)

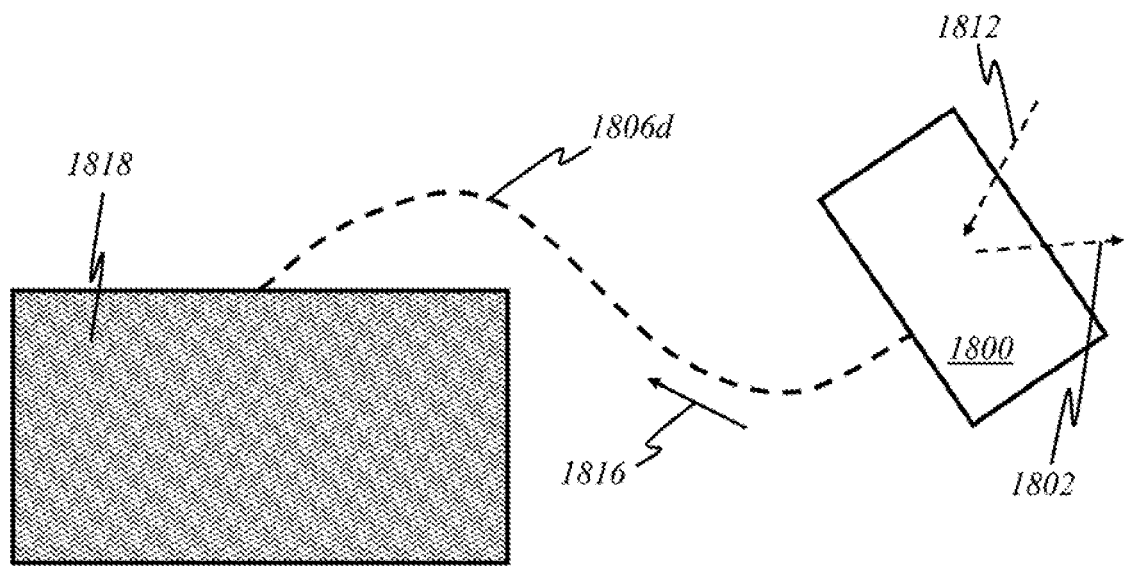
FIG. 24 Whole view (2) (without wire)

SYSTEM FOR SCREENING AND DIAGNOSIS OF SKIN CANCER

FIELD OF THE INVENTION

This invention relates to apparatus and method for detection of cutaneous cellular mass utilizing multiple techniques, covering electronics, optics and imaging techniques. More particularly, this invention is related to detecting (a) abnormal growth of tissues inside the body, (b) their types, (c) their dimensions, and (d) their location from outside the body (through non-invasive contact or non-contact with the body). More specifically, this invention is related to the means to detect abnormalities of tissue growth inside the body, their types, dimensions, and location from outside, more particularly the early diagnosis of the cancer, especially melanoma skin cancer. This invention also relates to a medical device that emits electromagnetic waves of varying wavelengths (a.k.a. frequencies), and detects waves returned to the device.

BACKGROUND OF THE INVENTION

The human skin is a multifunctional organ of the body that provides protection, temperature regulation, sensory perception, excretion, and vitamin production. It is made of two major layers: the epidermis and the dermis (with the hypodermis under that). The epidermis is the outermost layer of the skin. The topmost layer of the epidermis is composed of dead cells that are continually being worn off. The epidermis has some nerve cells but no blood vessels. Cells in the deepest layers are nourished by diffusion from blood capillaries extending to the upper layers of the dermis, the layer underneath the epidermis. The dermis provides cushion to the body and flexibility to the skin. It includes nerve endings, blood vessels, sweat glands, and hair follicles. The hypodermis (subcutaneous tissue) lies underneath the dermis and is not part of the skin. It contains much fat and connects the skin to other parts of the body, such as bone and muscle.

Skin cancer is the uncontrolled growth of abnormal skin cells resulting in malignant tumors. It is most often caused by ultraviolet radiation or genetic defects. It is the most common form of cancer in the United States, where over 3.5 million cases of skin cancers are diagnosed each year and increasing over time. The most common type, basal cell carcinoma, is rarely fatal but can be disfiguring. The second-most common type, squamous cell carcinoma, is more fatal, killing about 2% in 2012.

Malignant melanoma is a rarer type of skin cancer mostly caused by UV radiation, but it is the most dangerous type. It is a tumor of melanocytes, which are found in the epidermis. One person dies of melanoma every 57 minutes. The number of melanoma cases and the rate of mortality from melanoma have been increasing over the years. Even if a patient survives melanoma, the likelihood of developing new melanoma is nine times greater than for the general population. Concern for skin cancer generally increases as one grows older and accumulates sun exposure over one's lifetime. More than 90 percent of the visible changes commonly attributed to skin aging are caused by the sun. Melanoma is thus a type of skin cancer that merits treatment as soon as it is detected.

When allowed to advance and spread to other parts of the body, skin cancer can result in disfigurement or death. Treatment is possible, but societal costs are high. About 40% of the annual cost for melanoma in patients 65 or older ($249 million) goes to treating advanced, stage IV cancers. The total cost for treating melanoma was $2.36 billion in 2010. The overall 5-year survival rate for patients whose melanoma is detected early is about 98 percent in the U.S. But the survival rate falls to 62 percent when the disease reaches the lymph nodes and 15 percent when the disease metastasizes to distant organs. Thus, early detection is paramount to extended survival and prevention of further damage. The earlier skin cancer is detected, the easier it is to treat successfully. It is important to have a means to screen oneself often or investigate suspicious areas of the skin to catch the cancer early and increase their chances of survival. Unfortunately, there exists no device on the market that one may inexpensively use to regularly screen for skin cancer at home.

Currently, there are recommended methods for detection of skin cancers, including skin self-examination and physician's full-body skin examination. Self-examination involves a head-to-toe examination of the skin for lesions that might be cancerous or precancerous. However, it is often difficult to tell whether a lesion is merely a mole or developing skin cancer. Melanomas often look like ordinary moles, and some melanomas do develop from ordinary moles. Moreover, mere self-examination of the surface of the skin cannot determine how far a potential case of skin cancer has spread under the skin and into the body. Dermatologists can look for signs of skin cancer, but a lesion on the skin that the physician suspects is cancerous will be biopsied-some skin is removed for evaluation by a pathologist. This is a multi-step, invasive process that requires a waiting period for results. The process may be more challenging if a lesion is located in a sensitive or delicate area. Thus, it is difficult to determine if and when a lesion is cancerous or is transforming into a case of melanoma.

Most suspected melanomas detected during screening programs are not actually melanoma, leading to false-positive results. These results lead to biopsies or surgery, possibly resulting in unnecessary overtreatment. One study found that sufficient proof does not yet exist to prove that self-examination or whole-body skin exams reduce deaths from skin cancer. However, it is contemplated that routine self-screening combined with the accuracy of a biopsy may contribute to preventing deaths from skin cancer.

It would be useful and desirable to have a portable, non-hazardous and non-invasive device that anyone can use to screen themselves for skin cancer without the need to rely on purely surface symptoms and physician visits. The present invention provides for a device that uses multispectral imaging using broadband sources and/or multiple coherent sources to produce high-resolution, three-dimensional images of cutaneous tissue and to detect potential skin cancers on and underneath the surface of the skin with high accuracy. Quick delivery of images and results in the privacy of one's home allows the user to interpret the results and decide whether to invest further time and energy by visiting a dermatologist, who can determine whether a biopsy is needed to answer questions on the penetration stage of the cancerous lesion.

SUMMARY OF INVENTION

The present invention aims to overcome problems associated with current technologies by providing a method and device that is friendly to users and makes screening and diagnosis of skin cancer more sensitive, more rapid, non-invasive, and less costly, allowing for early detection of emerging tumors through routine self-examination.

The following presents a summary of the invention and a basic understanding of some of the aspects of the invention. It is not intended to limit the scope of the invention or provide critical elements of the invention. Its sole purpose is to present some of the features of the invention in a simplified form as a prologue to the more detailed description presented later.

It is an object of this invention to allow skin cancer screening and diagnosis to be non-invasive.

It is an object of this invention to encourage routine skin cancer screening which is self-operable, more private, easier to use, yet cost-effective.

It is an object of this invention to raise the accuracy of diagnosis and reduce the rate of false positives and false negatives.

It is an object of this invention to incorporate several techniques detecting the cancer tissues in order to achieve high accuracy.

BRIEF DESCRIPTION OF DRAWINGS

For a better understanding of the aforementioned aspects of the invention and additional aspects and embodiments thereof, reference should be made to the Detailed Description, below, in which reference numerals refer to corresponding parts throughout the figures under Drawings.

FIGS. 1A-1D show a progression of a lesion that may occur in skin.

FIG. 2 shows a block diagram illustrating the basic operational parts of the present invention.

FIG. 3A shows a sample graph of an example of an absorption spectrum.

FIGS. 4A-4G show various arrangements of light sources that may be implemented in accordance to the present invention.

FIG. 5A shows a schematic of basic parts of a light detector.

FIGS. 5B and 5C show various arrangements of detectors that may be implemented in accordance to the present invention FIGS. 6A-6E show various arrangements of sources and detectors that may be implemented in accordance to the present invention.

FIGS. 7A and 7B show schematics of a preferred "flat" embodiment in an angled view.

FIG. 8B shows a schematic of another preferred "flat" embodiment in a cross-sectional view.

FIG. 8C shows a schematic of the connector component of the embodiment of FIG. 8B.

FIG. 12A shows a schematic of a preferred "non-contact" embodiment in a top view.

FIGS. 12B and 12C show schematics of the preferred "non-contact" embodiment in a front view.

FIG. 13A shows a schematic of another preferred "non-contact" embodiment in a top view.

FIGS. 13B and 13C show schematics of the preferred "non-contact" embodiment of FIG. 13A in a front view.

FIG. 14 shows a cross-sectional schematic of a "semi-contact" embodiment that uses temperature differentials to detect lesions.

FIG. 15 shows a schematic illustrating the effect of applying a heating stress on skin using the embodiment of FIG. 14.

FIG. 16 shows a schematic of an optical-fiber cable used in the present invention.

FIGS. 18-24 show a whole view of schematics of operational parts implemented in preferred embodiments of the present invention.

DETAILED DESCRIPTION OF THE INVENTION

Figure 3B:
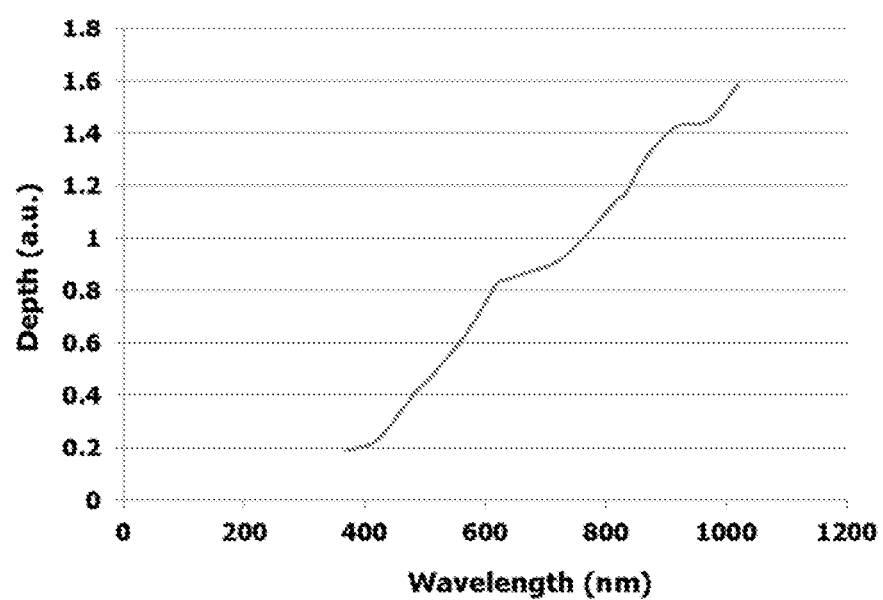
FIG. 3B shows a sample profile of wavelength of light emitted vs. depth of dermis.

Reference numerals refer to corresponding parts labeled throughout the figures. The embodiments described herein pertain to a device that detects and images cutaneous cellular mass through optical techniques. The embodiments pertain to methods and apparatuses for screening and diagnosis of skin cancer.

As used herein, the term "area of interest" and "area of concern" refer to parts of bodily tissue where cancer cells are suspected or known to be. For example, a patient may spot a discolored and lumpy area on his or her skin. The general area where the lump was would be an area of concern because it is suspected that cancer cells may be developing in the lump. In particular, a "tumor" is an abnormal growth of cells, especially malignant neoplasms that invade nearby cells (cancer).

As used herein, the term "biomass" refers to a total mass or volume of organic matter, typically from the human body. It could be an entire organ or portion thereof, a section of skin, lymph or blood vessels present throughout the body, and/or a collection of cells, ex vivo or in vivo. In the present invention, discussion of "biomass" is aimed primarily at skin and layers of the skin, including the epidermis, dermis, hypodermis, as well as organelles and other components present therein.

As used herein, the terms "light," "radiation," "electromagnetic wave" and "electromagnetic waves" are interchangeable, unless specified. "Broadband" light refers to light carrying waves of varying wavelengths, typically a range of wavelengths (or a band). Broadband light is generated by a broadband source, which may emit multiple ranges of wavelengths to selectively emit multiple groups of wavelengths. On the other hand, "uniband" or "coherent" light refers to light having one particular wavelength or a narrow range of wavelengths.

As used herein, the terms "reflect," "refract," "scatter," "diffract" and "fluoresce" refer to the behavior of light waves upon interacting with another material. "Reflect" refers to a process in which light and other electromagnetic radiation are cast back after impinging on a surface. "Total internal reflection" occurs when light strikes a medium boundary at an angle larger than a particular critical angle with respect to the normal to the surface. "Refract" refers to change in direction of electromagnetic radiation in passing from one medium to another. The optical density of a medium is the refractive index, an inherent value of the medium. "Refract" refers to change in direction of electromagnetic radiation in passing from one medium to another. "Fluoresce" refers to exhibiting fluorescence, which is refers to emission of electromagnetic radiation stimulated in a substance by the absorption of incident radiation. "Diffract" refers to exhibiting diffraction, which refers to a deviation in the direction of a wave at the edge of an obstacle in its path. "Scatter" and "diffract" are interchangeable.

As used herein, the term "panel" associated with light sources and light detectors refer to a continuous and generally transparent surface that emits or receives light. Multiple light source and light detector units are housed under a panel. This is distinguishable from a mere collection or array of sources or detectors. An array is an arrangement of sources or detectors, but each source or detector is discretely placed, not connected to one another or housed under one transparent pane.

The terminology used in the descriptions of the embodiments herein is for the purpose of describing particular embodiments only and is not intended to limit the claims. The singular articles "a," "an" and "the" are intended to include the plural forms as well, unless the context clearly indicates otherwise. It will also be understood that the term "and/or" refers to and encompasses any and all possible combinations of one or more of the associated listed terms. Similarly, the conjunction "or" is not necessarily mutually exclusive.

References will now be made in detail to embodiments, accompanied by numerals that correspond to appropriate parts of the figures. Examples will be provided to illustrate the various ways the present invention may be utilized. Specific details will beset forth to provide a thorough understanding of the present invention. However, it will be apparent to those with ordinary skill in the art that the present embodiments may be practiced without these specific details. In other instances, known methods, procedures and components have not been described in detail to avoid unnecessarily obscuring aspects of the embodiments.

When a beam of light interacts with a material, e.g., a tumor, part of it is transmitted, part it is reflected, and part of it is diffracted (scattered). Various scattering types result based on the size of the particle and the wavelength of the incident radiation, though it occurs at all wavelengths of the electromagnetic spectrum. The equation to determine the scattering type is described by: $\alpha=\pi D_p/\lambda$, where $\pi D_p$ is the diameter of the particle, and $\lambda$ is the wavelength of the incident radiation. The value of a determines the domain of the scattering type. If $\alpha<<1$, it is Rayleigh scattering, in which the particle is very small compared to the wavelength. If $\alpha\approx1$, it is Mie scattering, in which the particle is about the same size as the wavelength. If $\alpha>>1$, it is geometric scattering, in which the particle is much larger compared to the wavelength. Particles with sizes very small ($r<\lambda/10$) compared to the wavelength of incident radiation, scatter uniformly into both the forward and backward direction. Over 99% of the scattered radiation has the same frequency as the incident beam. Thus, incident light that has diffracted is identifiable by its wavelength. Mie and Rayleigh scattering types exhibit this type of behavior. A small portion of the scattered radiation has frequencies different from that of the incident beam: Raman and Brillouin scattering have forms of inelastic scattering. Fluorescence of light occurs where a substance that has absorbed light or other electromagnetic radiation and emits light, which is lower energy than the absorbed radiation, unless the absorbed electromagnetic radiation is sufficiently intense. The two-photon absorption process helps fluorescing light emit radiation having higher energy after absorption. In the present invention, single-photon absorptions and/or two-photon absorptions can be used to further verify the type and dimensions of the cancer tissue. According to this invention, two-photon absorptions help detect the cancer cells that exist deeper in the body and identify the size and type of tissues.

Reflection or refraction of light may occur whenever light travels from a medium of a given refractive index into a medium with a different refractive index. Total internal reflection occurs when light strikes a medium boundary at an angle larger than a particular critical angle with respect to the normal to the surface. If the refractive index is lower on the other side of the boundary, no light can pass through and all of the light is reflected. The critical angle is the angle of incidence above which the total internal reflection occurs. Diffuse reflectance may occur at boundaries of different substances or particles, where light is partially reflected (few percent intensity) while passing the boundary. Refraction of light is described by Snell's law: The angle of incidence $\theta_1$ is related to the angle of refraction $\theta_2$ in another medium by $\sin\theta_1/\sin\theta_2=n_2/n_1$ where n is the refractive index.

Photon propagation in tissue can be further described by five variables: 3 spatial coordinates to describe the position (Cartesian coordinates) and 2 directional angles to describe the direction of travel (spherical coordinates). The relationship between penetration depth of light and its wavelength can be described by: Effective penetration depth $1/\mu(\text{eff})$; $\mu(\text{eff})$ effective attenuation coefficient=$[3\mu(a)\times(\mu(a)+\mu(s'))]^{0.5}$; where $\mu(s')$=attenuation coefficient=$\mu(s)(1-g)$; $\mu(a)$= absorption coefficient; $p(s)$=scattering coefficient; and g=anisotropic properties. The latter optical properties are measurable or known values for a type of tissue material.

FIG. 1 illustrates the stages of malignant melanoma from cross-sectional viewpoints of a volume of human skin. The block of skin on the upper left diagram is normal skin, with no cancerous indications. The block of skin on the upper right shows a lesion 102 that is visible and has rooted itself in the epidermis 104. In this illustration, it can be seen that lesion 102 is about 5 mm wide. At this stage, it is difficult to tell whether it is a cancerous lesion, a liver spot, or a mole. However, the bottom figures illustrate the progression of lesion 102 as it spreads wider and deeper into the dermis 106 and perhaps the hypodermis 108 over time. The present invention allows three-dimensional imaging of lesion 102 or area of interest that may have damaged the skin internally and determine whether that area of interest is likely to be cancerous.

FIG. 2 is a block diagram illustrating the overarching concept of the present invention. At time to, a light source 200 emits light 202 of a particular wavelength ("uniband") or varying wavelengths ("broadband") into a skin tissue 204. In some embodiments, each source 200 is lined up in a two-dimensional fashion to create an array of sources (see below). Each source 200 may emit a certain wavelength. In some other embodiments, sources emitting the same wavelength may be grouped into larger panels. In yet other embodiments, each source 200 may emit a range of wavelengths. A source driver 206 drives source 200 and selects the pulse duration to be operated. Source 200 can be operated in continuous wave (CW) or pulse operation based on the necessities, and it converts electric signals to optical signals. A controller 208 receives instructions to provide signals to a source driver 136, which operates a specific source. Alternatively, controller 208 also receives instructions to operate the sources having specific wavelengths and/or specific ranges of wavelengths in either pulse or CW operation. According to this invention, alternatively, controller 208 can be operated and are instructed by one or more circuit blocks (not shown here) to operate desired source, desired wavelength(s), desired pulse-width/CW, desired intensity, or a combination thereof.

Light 210 returns as a reflection, or scatters and comes back as diffracted, refracted, or scattered light. At time $t_1$, a detector 212 receives returned light 210 of a certain wavelength. Detector 212 converts light 210 into electrical signals, which are sent to a signal amplifier 214. A digitizer 216 turns the amplified signal into digital form. A processing element ("processor") 218 performs calculations that can create three-dimensional images from two-dimensional images. Processor 218 produces other important data. For instance, it determines the location of areas of concern by deriving times of flight $t_1$-$t_0$ and the size of areas of concern by comparing images from light of different wavelengths. Although some absorption of emitted light 202 occurs, if an object has a size smaller than the wavelength of light hitting it, diffraction and scattering of the light occurs. On the other hand, if an object has a size larger than the wavelength of light, the object reflects the light. Thus, processor 218 may determine the size of potential tumors by collecting images based on light 202 of varying wavelengths. Processor 218 then sends relevant information to a display screen 220 for a user to read.

According to this preferred embodiment, processor 218 operates the transmission elements and the receiving elements (not shown here specifically), and processes the receiving signals based on a build-up algorithm, described later. The transmission elements (not shown here specifically) comprise controller 208, driver 206, and source 200. Processor 218 instructs the transmission elements and receiving elements, based on its determination of how to operate the source and which part of receiving elements should be processed.

By way of example and without any limitation, in FIG. 2, the source can be operated in various ways using blocks ("components")? having the functionality to select the source, wavelength, pulse/CW, and source intensity, and in various ways processor 218 can operate the transmitter elements and receiving elements, as instructed by software, either embedded into processing unit 218, and/or separately operated by a computing unit with or without display element 220 externally interfaced with processor 218.

According to this invention, alternatively, the components as shown in FIG. 2 may be grouped in different locations. The dotted lines above the block diagram indicate how the components may be grouped together. In some embodiments (Embodiment A), light sources 200 and detectors 212 are placed together in a handheld device separate from the module containing processor 218 along with the other components illustrated. The handheld device is henceforth referred to as the "user end"; the latter module is henceforth referred to as the "processor end". During operation, the user directly manipulates the handheld "user end" device over the skin, emitting light 202 and detecting returning light 210. Light 210 that returns to the user end is sent to the processor end (containing processor 218) through electrical, optical, or wireless channels (see FIGS. 18-24). The transmitted signals are then amplified, processed, and may be displayed on screen 220.

According to this invention, in some other embodiments (Embodiment B), light sources 200, detectors 212, and processor 218 are in the processor end. Initial emission and later collection of light are both performed at the processor end. Light 202 emitted from sources 200 and light 210 returned to the detectors 212 propagate through an optical-fiber cable. At the other end of the optical cable is a handheld device on the user end, which the user places, moves, or otherwise manipulates over skin tissue 204. This device delivers light 202 emitted and carried via optical means from sources 200, and then collects and focuses returned light 210 for transmission back through the optical cable to detectors 212. Electrical or wireless means are not used in these embodiments because only optical signals travel between the user end and the processor end.

In yet other embodiments (Embodiment C), light sources 200, detectors 212, and processor 218 are in one device: the user end. All light generation, data gathering, processing, and imaging are done within the handheld device. End result of operation, such as images and other data, are transferred via electrical, optical, or wireless means to display screen 220 or another device, such as a mobile device or a monitor of a computer. Other means of implementation and descriptions of accompanying figures are disclosed below to reveal a closer look at the arrangements of sources 200 and detectors 212.

A diffraction pattern, i.e., an interference pattern that propagates uniformly when a wave or a series of waves undergoes diffraction, results if an obstacle has a size smaller than the wavelength of optical wave encountering the object. The pattern provides information about the frequency of the wave and the structure of the material causing the diffraction. An interferometer can be used to detect the nature of the diffraction pattern.

Functions of above-described embodiments of the handheld device are driven by software programs. There are several main functions. One function of the device can perform a rough spatial scan of the skin tissue to locate possible areas of concern. The rough spatial scan is performed with variation of intensity (thus varying the depth) per unit area per unit time. The scan spatially covers the skin tissue by emitting broadband light, coherent, or incoherent sources, and then collecting any returning light. If light returns, the reflected light has varying patterns—direct reflection, diffraction, fluorescence-based on the size (early stage or later stage), characteristic of the cells (mere calcification, hard-shelled tumor or soft-shelled tumor) the emitted light struck, and the nature of the emitted light. The scan also covers the tissue depth-wise by varying the intensity and/or wavelength of the emitted light. The scan detects tumor-like substances by matching the returning light with known diffraction patterns or spectral profiles of cancerous lesions. It can then continue with a detailed scan and iterations with varying optical parameters in the areas of concern for further analysis and obtaining results, which may include a high-resolution scan, determination of depth and location, construction of a three-dimensional image, and identification of the type of the tissue substance (normal, healthy tissue vs. harmless calcification vs. early-stage tumor). Optical parameters include wavelength, energy fluence rate (flux over time), pulse rate, absorption coefficient, scattering coefficient, refractive index, scattering phase function. Light propagation in scattering and absorbing media can be defined with respect to radiative transfer.

According to one-dimensional transport theory, light propagation in scattering and absorbing media can be defined by integro-differential equation of radiative transfer, assuming 1) optical properties can be measured, 2) light propagation is restricted to +x or −x directions, and 3) the tissue light interacts with is homogenous and isotropic. Optical properties under this model include: $\mu_{a1}$=absorption coefficient for 1D geometry, [m$^{-1}$]; $\mu_{s1}$=scattering coefficient for 1D geometry, [m$^{-1}$]; σ=backscattering coefficient where $\mu_{s1}p(+,-)=\mu_{s1}p(-,+)$, [m$^{-1}$]; $p(\hat{x}, \hat{x}')$=scattering phase function where $\hat{x}$ and $\hat{x}'$ are directional unit vectors; F=(x)= photon flux in +x direction, [Wm$^{-2}$]; F−(x)=photon flux in −x direction, [Wm$^{-2}$]; E=incident (laser) irradiance, [Wm$^{-2}$]. Accordingly, $\mu_{a1}$ dx=probability that a photon is absorbed when traversing infinitesimal distance dx; $\mu_{s1}$ dx=probability that a photon is scattered into either +x or −x direction when traversing infinitesimal distance dx; $p(\hat{x}, \hat{x}')\mu_{s1}$ dx=probability that a photon is scattered from the direction of propagation $\hat{x}'$ into direction $\hat{x}$ when traversing infinitesimal distance dx. The following equations hold true under this one-dimensional transport theory.

1D transport equations (1) and (2):

$$F_+(x+dx) - F_+(x) = -F_+(x)\mu_{a1}dx - \quad (1)$$
$$F_+(x)\mu_{s1}dx + F_+(x)p(+,+)\mu_{s1}dx + F_-(x)p(+,-)\mu_{s1}dx$$

$$\frac{dF_+(x)}{dx} = -F_+(x)(\mu_{a1}+\mu_{s1}) + F_+(x)\mu_{s1}p(+,+) + F_-(x)\mu_{s1}p(+,-) \quad (2)$$

Backscattering coefficient (3):

$$\sigma = \mu_{s1}P(-,+) = \mu_{s1}P(+,-) \quad (3)$$

Differential photon flux in +x and −x directions, equations (4-1) and (4-2):

$$\frac{dF_+(x)}{dx} = -(\mu_{a1}+\sigma)F_+(x) + \sigma F_-(x) \quad (4\text{-}1)$$

$$-\frac{dF_-(x)}{dx} = -(\mu_{a1}+\sigma)F_-(x) + \sigma F_+(x) \quad (4\text{-}2)$$

1-D fluence equations (5) and (6), where m=$(\mu_{a1}+\sigma)/\sigma_b$, and b=$\sqrt{m^2-1}$:

$$F_+(x) = E\frac{m\sinh[b\sigma(D-x)] + b\cosh b\sigma(D-x)]}{m\sinh(b\sigma D) + b\cosh(b\sigma D)} \quad (5)$$

$$F_-(x) = E\frac{\sinh[b\sigma(D-x)]}{m\sinh(b\sigma D) + b\cosh(b\sigma D)} \quad (6)$$

Energy fluence rate can be related to depth or distance by equation (7), where L=radiance, [W/m$^2$*sr]; p=phase of scattering function; S=source of power generated at r in direction of $\hat{s}$:

$$\frac{dL(r,\hat{s})}{ds} = -\mu_a L(r,\hat{s}) - \mu_x L(r,\hat{s}) + \mu_x \int_{4\pi} p(s,\hat{s}')L(r,\hat{s}')d\omega' + S(r,\hat{s}') \quad (7)$$

Another function of the invention is to determine the wavelengths of the light before it is emitted and whether different wavelengths of light are emitted simultaneously. Individual (uniband) wavelengths may be emitted, scanning the entirety of the target skin tissue one wavelength at a time. With time and effort expended up front, this would narrow down the wavelengths that respond to any potential areas of concern. On the other hand, a range or broadband wavelengths may be emitted. Depending on the range of wavelengths, this method would provide a rough analysis in which a larger scope of potential areas of concern would be collected. The device may further allow measurement of temperature differentials of the skin's surface (see FIG. 15).

FIG. 3A illustrates an example of an absorption spectrum 300 of light by an arbitrary mass or volume of tissue. As the wavelength of light changes, so does the level of absorption by a material. Shown are two arbitrary wavelengths, $\lambda_1$ and $\lambda_2$. At $\lambda_1$, absorption of electromagnetic wave having wavelength $\lambda_1$ increases. This is an effective wavelength to target with a light source because some absorption is desired to distinguish between emitted light and reflected light, which would have a lower relative intensity than that of emitted light. At $\lambda_2$, absorption of electromagnetic wave having wavelength $\lambda_2$ is high. It may not produce useful images if most of the light is absorbed and not returned to a detector. Based on absorption spectra of particular materials of interest, such as those of precancerous and cancerous nonmelanoma cells and melanoma cells, the light sources are configured in a way that emit a range encompassing relevant wavelengths that would produce useful data. In some wavelengths, either lower than $\lambda_1$ and/or longer than $\lambda_2$, the specific material(s) does not have an absorption and is transparent to those wavelengths. FIG. 3B is an example profile of an ex vivo measurement of depth of the dermis based on wavelength of light emitted. The present invention depends on the variability of depth penetration with wavelength. It is necessary for locating potential tumors and creating three-dimensional images to relate the wavelength of emitting light and the depth it reaches relative to the surface of the skin.

Light sources may be light-emitting diodes, lasers, or broadband sources. LEDs would have a broader wavelength spectrum, but they are less ideal for generating high-resolution, wavelength-specific data. Lasers offer greater precision and specificity of wavelengths, but their power output should be carefully controlled. Specifically, the full width at half maximum of the spectral width of the LED ($\lambda_1$) would generally be greater than that of a laser source ($\lambda_2$). Broadband sources may be better served by LEDs or other broadband sources created using tungsten lamp, for example, while coherent sources may be better served by lasers. Alternatively, according to this invention, broadband sources having broader spectrum than the LEDs, can also be used as source 200. Practical configurations of LEDs, broadband sources, and/or lasers as light sources will be apparent to those having ordinary skill in the art.

Figure 4B:
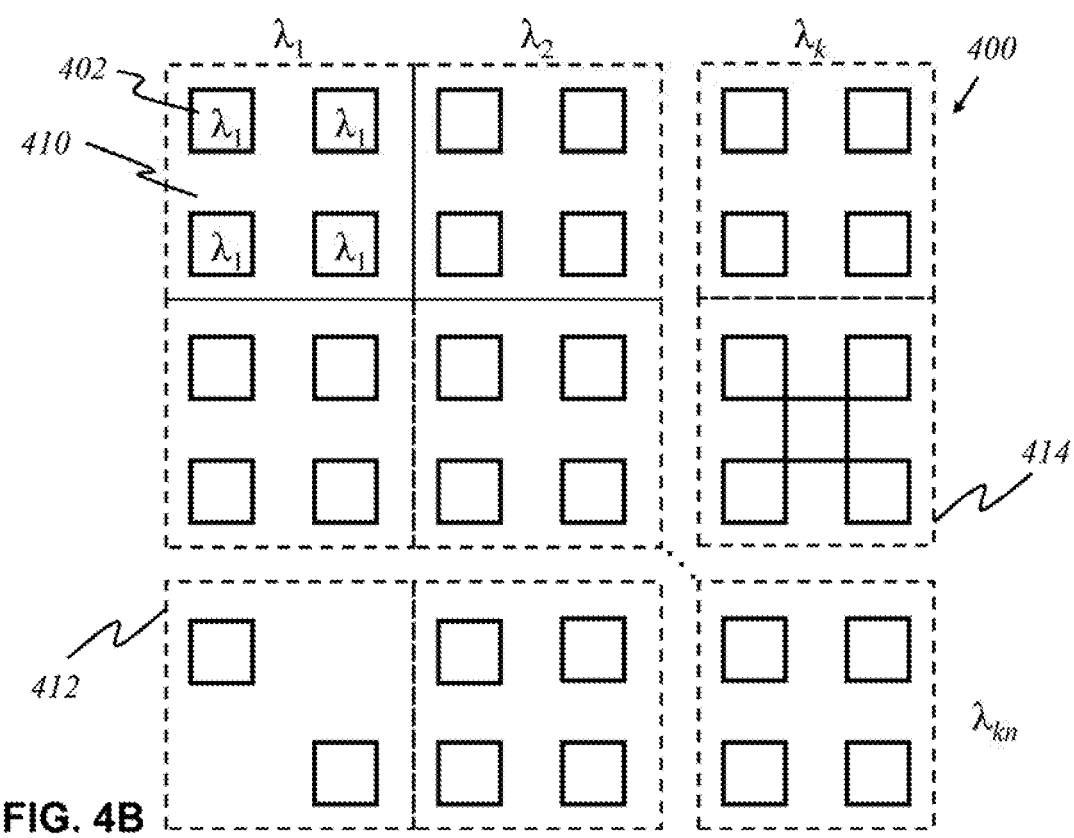

FIGS. 4A-4E and 4G illustrate arrays of light sources (emitters) in various configurations, in accordance to the present invention, wherein like parts are indicated by like reference numerals as used previously, so that repeated explanation is omitted here. FIG. 4A shows an embodiment wherein an array 400 of light sources has k×n array, representing k numbers of light source in x-direction and n numbers of array in y-direction, where k and n are positive integers. In the embodiment illustrated, each source in array 400, produces light of a certain wavelength; every source in array 400 is a unique source that emits light of relevant wavelengths. For instance, the first source 402 produces light of wavelength $\lambda_1$, an adjacent source 404 produces $\lambda_2$, a source 406 adjacent to that produces $\lambda_3$ and so on. No two sources emit the same wavelength in this configuration. The source emitting light of wavelength $\lambda_{kn}$ 408 is the "knth" source that produces a different wavelength. Alternatively, according to this invention, sources having more than one wavelength can be used in the array arrangement (not shown here).

According to this invention, in some other embodiments, shown in FIG. 4B, sources 402 that emit light having a certain wavelength are grouped together in panels 410. Multiple light sources with the same wavelength are employed to increase the resolution of data acquired from reflected or diffracted inbound light. Each panel 410 produces light waves of a unique wavelength, and the panels 410 are arranged in an array of k panels by n panels. Each panel 410 need not necessarily contain the same number of sources 402. There may be panels that contain a fewer or greater number of sources 402, depending on the characteristics and purpose of a particular wavelength. For example, panel 412 has two sources, and panel 414 has five sources.

Figure 4C:
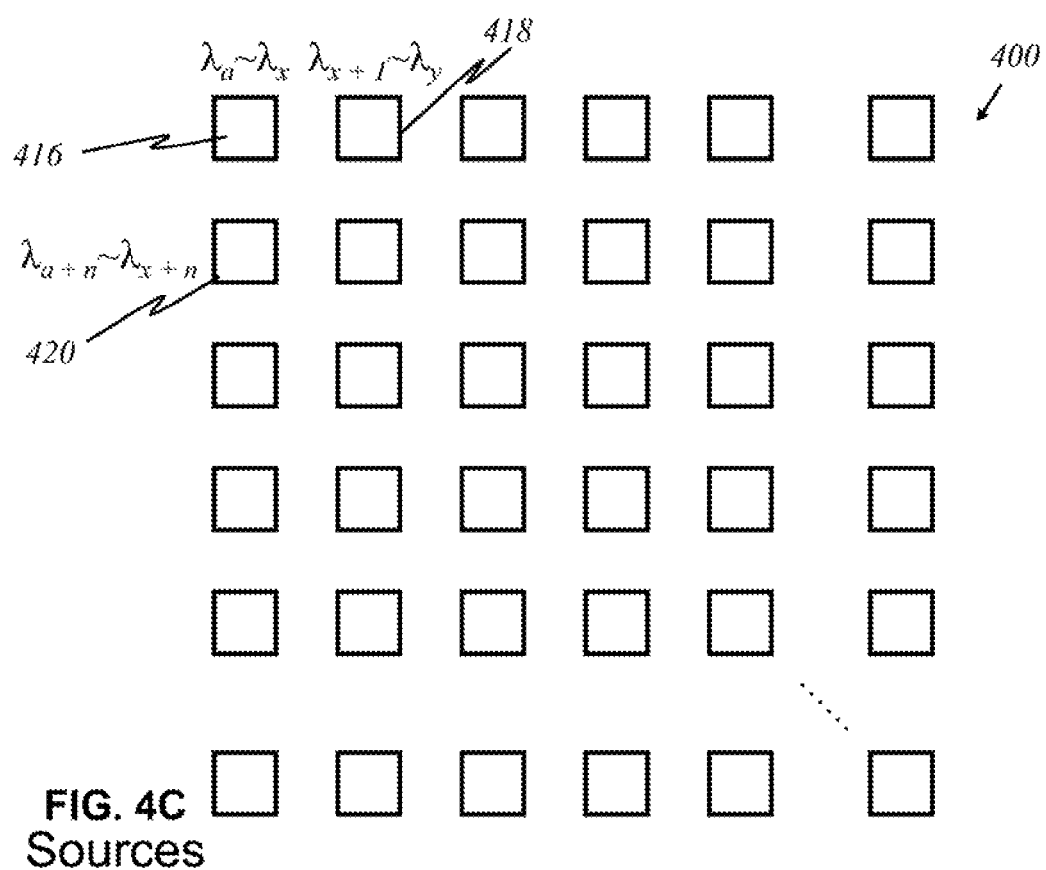

According to this invention, in yet other embodiments, shown in FIG. 4C, alternatively, light sources are broadband sources, which carry multiple signals—that is, emit a range of wavelengths. The ranges of wavelengths of emitted light differ from each other source, and they may overlap. For instance, a source 416 may emit light of wavelengths $\lambda_\alpha$ to $\lambda_x$, where a and x are arbitrary wavelengths. Another source 418 may emit $\lambda_{x+1}$ to $\lambda_y$, where x and y an arbitrary wavelengths, y being greater than x+1. Another source 420 may emit $\lambda_{a+n}$ to $\lambda_{x+n}$, where a+n is between a and x, and x+n is between x+1 and y.

Figure 4D:
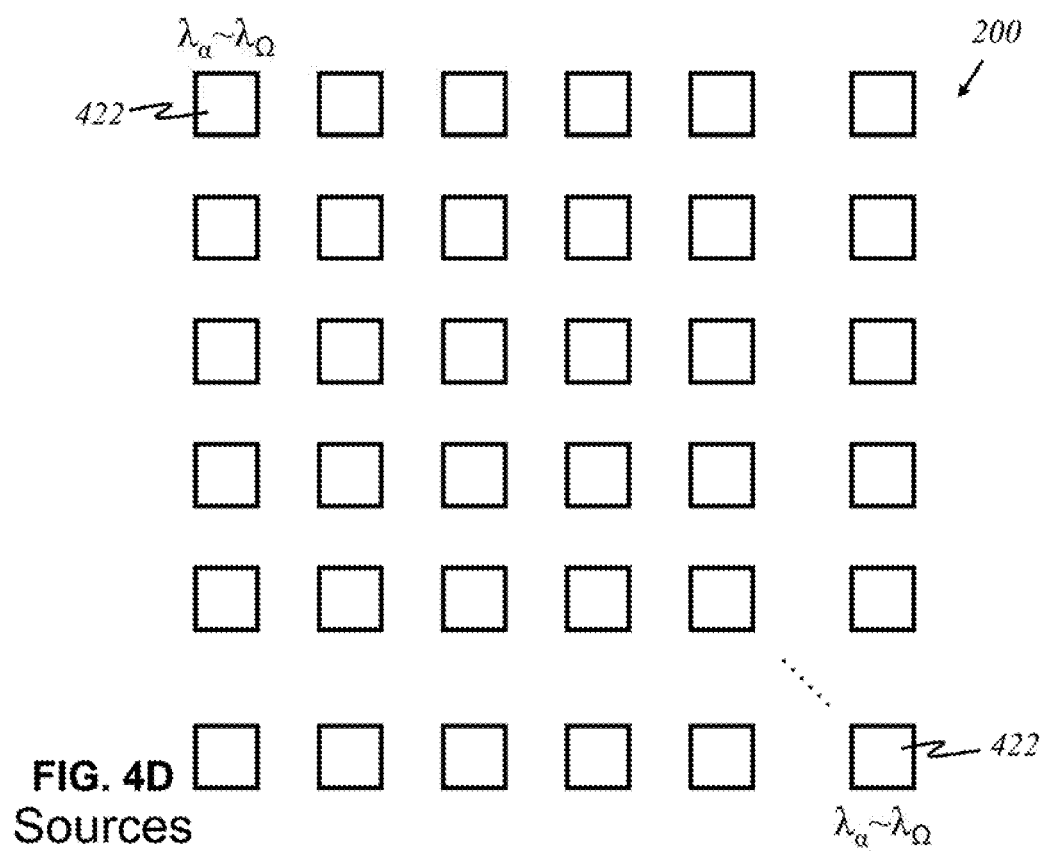
Figure 4E:
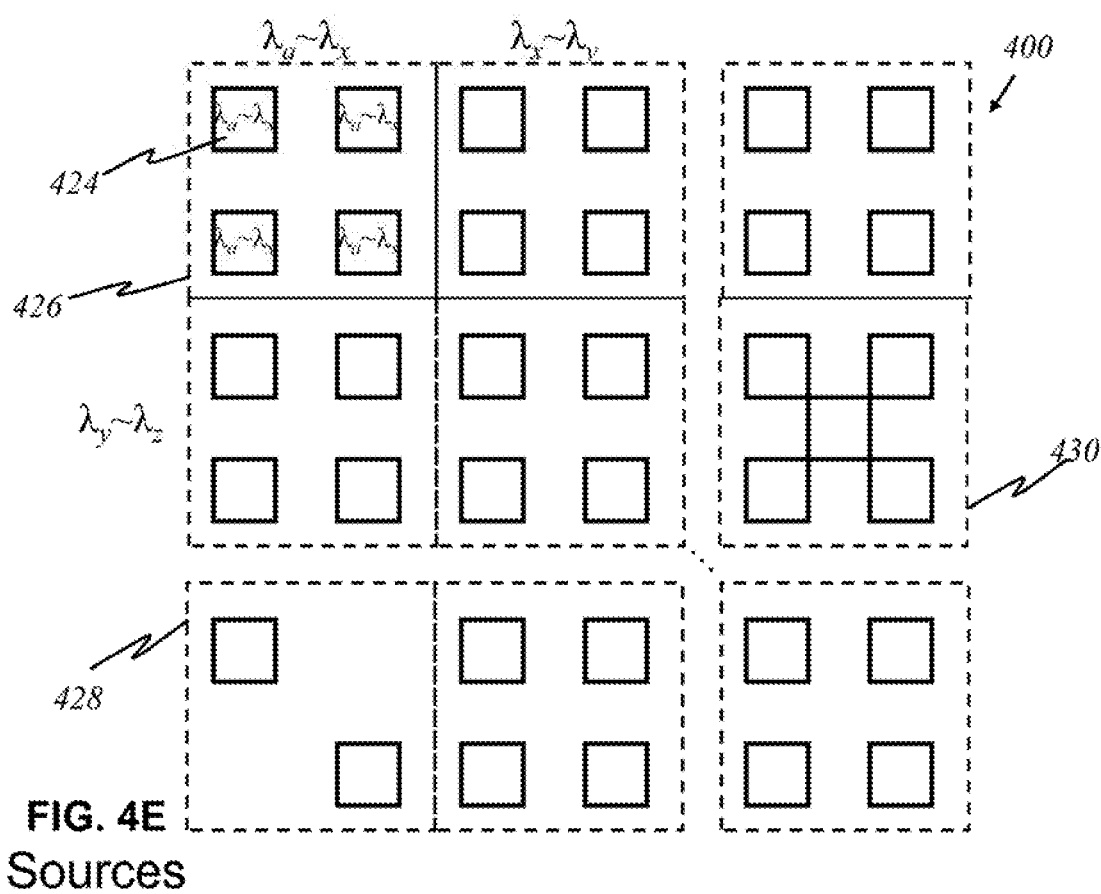

According to this invention, in other embodiments, alternatively shown in FIG. 4D, each source 422 may produce an entire range of desired wavelengths. An array 400 of light sources is shown in FIG. 4D wherein each source 422 produces light of wavelengths $\lambda_\alpha$ to $\lambda_\Omega$, where $\alpha$ is the smallest relevant wavelength desired, and $\Omega$ is the highest relevant wavelength desired. Such a source 422 may not emit all wavelengths between $\lambda_\alpha$ and $\lambda_\Omega$, only the relevant ones within that range. Broadband sources 424 may be grouped into panels 426, as shown in FIG. 4E. Similar to the arrangement in FIG. 4B, each panel 426 has sources 424 emitting light of the same range of wavelengths. The number of sources 424 may differ for each panel. There may be panels 428, 430 that contain a fewer or greater number of sources, depending on the characteristics and purpose of a range of particular wavelengths.

Figure 4G:
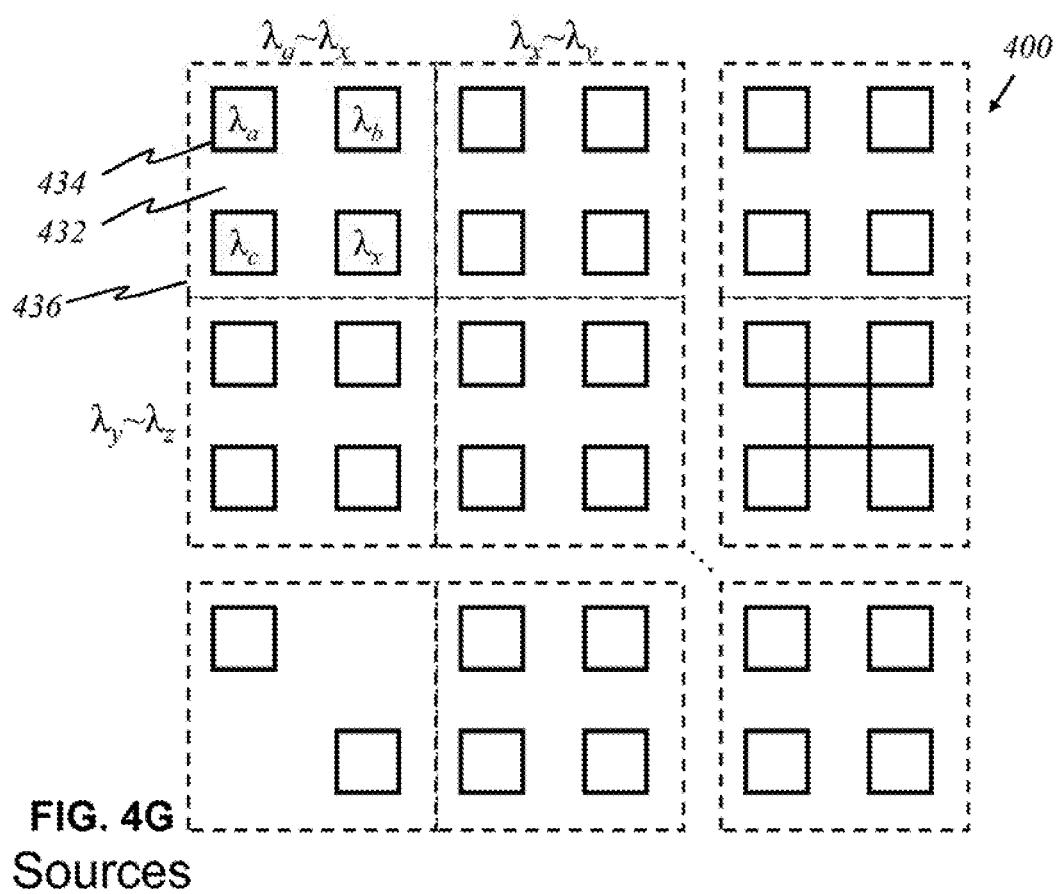

FIG. 4F is an illustration of a light source with a filter 432 that allows certain wavelengths to pass through while blocking other wavelengths in the preferred embodiment, according to this invention, wherein like parts are indicated by like reference numerals as used previously, so that repeated explanation is omitted here. Here, a broadband source 434 generating light 436 of multiple wavelengths $\lambda_1$ through $\lambda_5$ exits through filter 432. Filter 432 has openings that permit light of wavelengths $\lambda_1$, $\lambda_2$, $\lambda_3$, $\lambda_4$, and $\lambda_5$ to pass through. The result is effectively five light sources that each emits light that is no longer the original light generated by the broadband source. Its utility is illustrated in FIG. 4G, where light sources 434 are grouped together in panels. The number of sources may differ for each panel. There may be panels that contain a fewer or greater number of sources. Each panel comprises an underlying broadband source that produces light waves of multiple wavelengths. For example, underneath upper-left panel 436 is a broadband source that emits light of wavelengths $\lambda_a$ through $\lambda_x$, of which four distinct wavelengths $\lambda_a$, $\lambda_b$, $\lambda_c$, and $\lambda_x$ are relevant and of interest. By placing filter 432 over the source panel, one source is simply divided into multiple light sources that effectively function like the individual sources in FIG. 4A.

FIG. 5A illustrates the major components of a light detector 500 that registers light of particular wavelength(s) in a preferred embodiment, according to this invention, wherein like parts are indicated by like reference numerals as used previously, so that repeated explanation is omitted here. Each base detector component 502 is identical in that it detects the presence of light. To detect light of a particular wavelength or wavelengths, a filter 504 installed over the detector varies among each detector 500. Filter 504 blocks out other wavelengths, letting only particular wavelength(s) through. For example, if filter 504 is designed to allow only waves having wavelengths $\lambda_1$ and $\lambda_3$, light having other wavelengths, such as $\lambda_2$, are blocked. Thus, depending on the function of the filter, detector 500 becomes able to detect only desired wavelengths.

FIG. 5B shows a preferred embodiment of an array 506 of such detectors, the array having width k and length n, in accordance to this invention, wherein like parts are indicated by like reference numerals as used previously, so that repeated explanation is omitted here. Each detector 508 can only see and detect the presence of light of a certain wavelength: $\lambda_1$, $\lambda_2$, $\lambda_3$, etc. A detector that detects light of wavelength $\lambda_{kn}$ 510 is the "knth" detector that registers that wavelength. If light of a particular wavelength $\lambda_x$ reaches array 506 of detectors, only one detector will recognize it.

Figure 5C:
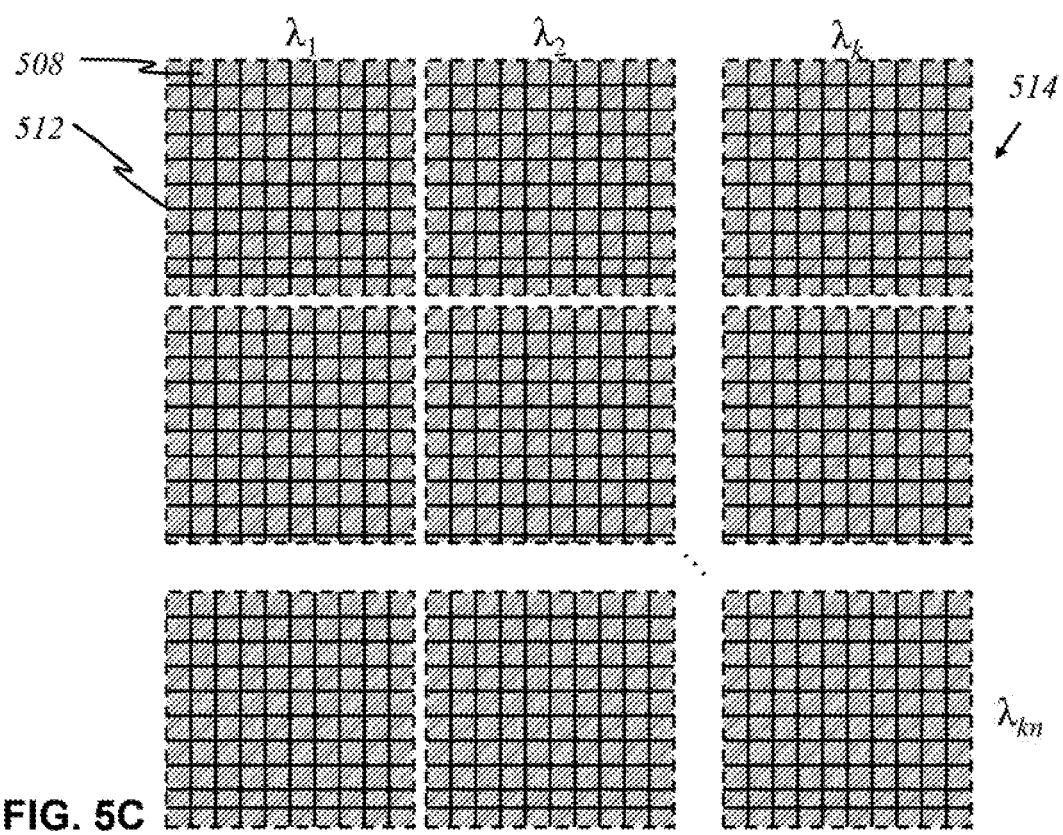

In another preferred embodiment according to this invention, alternatively, detectors 508 that see light of a certain wavelength are grouped together in panels 512, shown in FIG. 5C. Multiple detectors 508 are employed to detect the same wavelength increases the resolution of data acquired by reflected or diffracted light. Each panel 512 detects light of a particular wavelength, and the panels are arranged in an array 514 of k panels by n panels. In some embodiments, however, a filter is unnecessary for a base detector component to detect a particular wavelength; such a detector inherently has the capability to detect a unique wavelength or a narrow range of wavelengths.

Figure 6A:
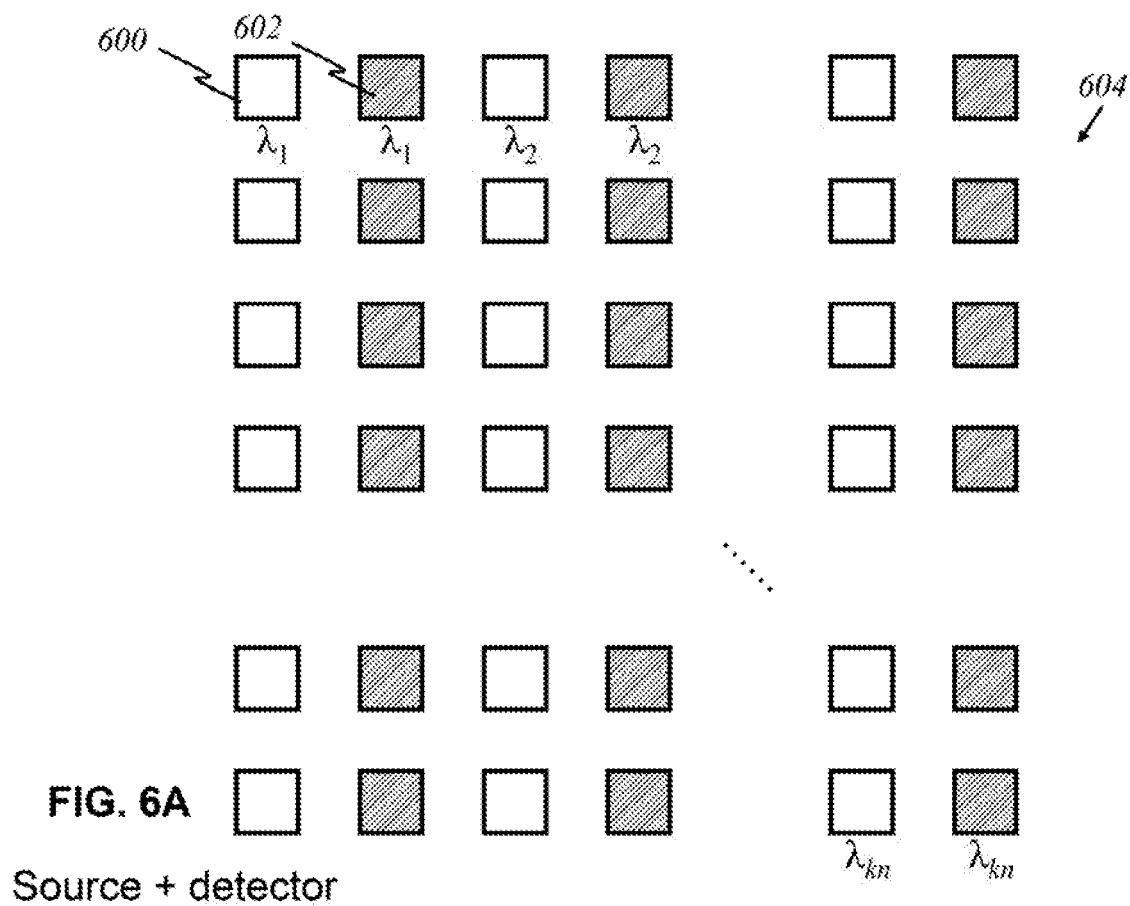

In yet other embodiments, rather than arranging light sources and detectors separately from each other, the sources and detectors can be placed together, as shown in FIGS. 6A-6E. In FIG. 6A, sources 600 that emit light of a certain wavelength and detectors 602 that detect light of a certain wavelength alternate on a source-detector array 604 of width 2k and length 2n.

Figure 6B:
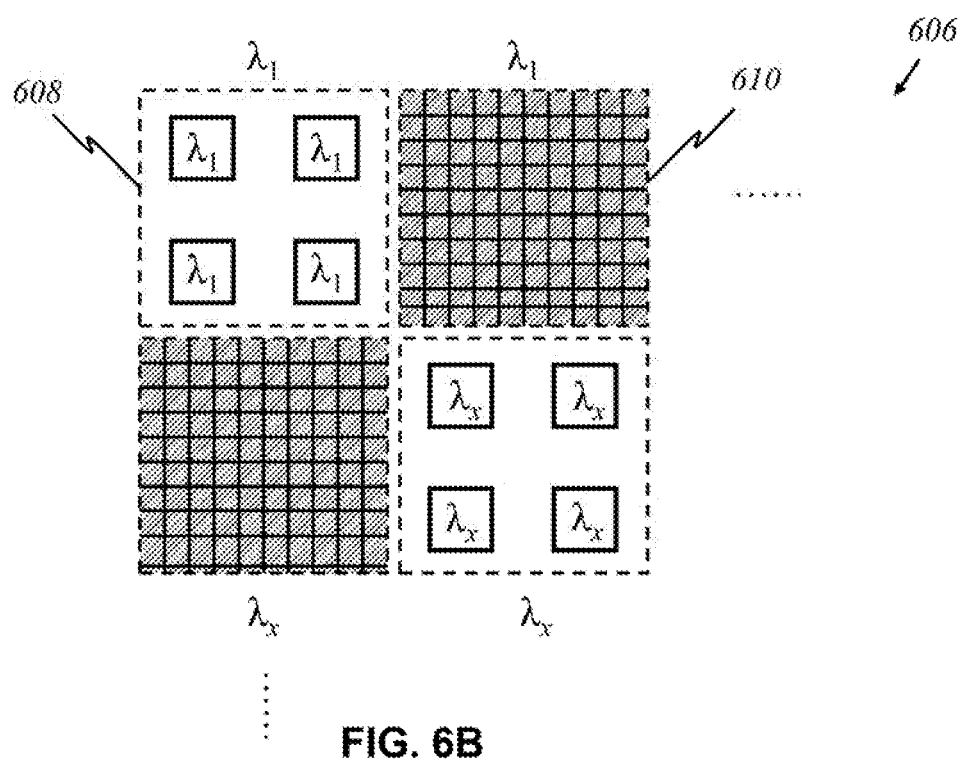

According to this invention, in another preferred embodiment shown in FIG. 6B, panels of multiple sources and detectors, rather than individuals, alternate in a source-detector-panel array 606. A panel comprising sources 608 emitting light of wavelength $\lambda_1$ is adjacent to a panel of detectors 610 that detect only $\lambda_1$. Other panels emitting and detecting light of arbitrary wavelength $\lambda_x$ are arranged similarly.

In another preferred embodiment shown in FIG. 6C, broadband sources and specific detectors are placed in alternating fashion on an array 612 of width 2k and length 2n. Similar to the arrays illustrated in FIGS. 4C-4E, broadband source 614 here may be capable of emitting a narrow range, a wide range, or any range of relevant wavelengths. Each detector 616 or group thereof, however, registers a particular wavelength. One having ordinary skill in the art is able to create further variations in arrangements of light sources and detectors.

Figure 6E:
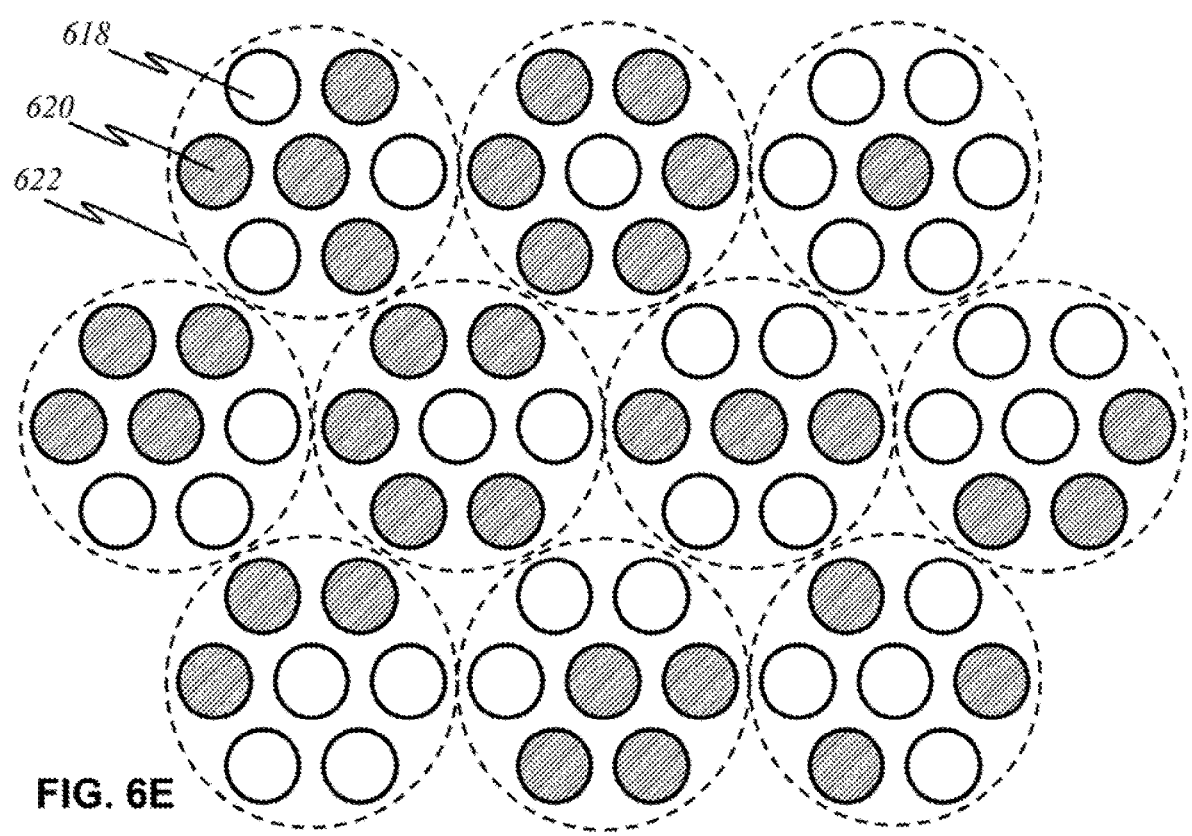

Other arrangements are possible in other embodiments. For instance. FIG. 6D illustrates sources 618 and detectors 620 of circular shape positioned in a space-efficient manner. FIG. 6E illustrates circular sources 618 and circular detectors 620 grouped in various combinations within panels 622. Similar to the previously described embodiments, sources 618 may be capable of emitting a narrow range, a wide range, or a range of relevant wavelengths. Each detector 620 or group thereof detects a particular wavelength. Other possible arrangements, shapes, and configurations (not shown here) will be apparent based on the aforementioned disclosures.

The various arrangements of the elements of the present invention manifested in a device will now be described in further detail. To emit light and detect reflected or diffracted light, light sources and detectors must be arranged in a way to emit appropriate wavelengths of light toward the user's skin and detect light that returns. The device can take numerous forms to provide such functions. In some embodiments, one general shape of the device could provide a detachable flat surface that interacts directly with the skin. In other embodiments, it could be a compact device that can flip open panes of sources and detectors. In yet another embodiments, it could measure temperature differentials after a heating stress. Other arrangements, features, structural dimensions, shapes, materials used, etc., allowing detectors to receive light reflected or diffracted from the epidermal and dermal tissue will be apparent to those having ordinary skill in the art.

FIGS. 7A and 7B are schematics showing a front view and an angled view, respectively, of a preferred embodiment of the user end of the device which has a flat surface 700 that makes direct contact with the skin ("flat contact embodiment"), according to this invention. In this embodiment, the device has a flat yet non-rigid surface and is connected to a mainframe (not shown here) via a cable 702, which represents a bundle of optical fibers, an electronic connection, or a wireless connection. The mainframe contains a processor and generates light signals or corresponding electrical signals to the handheld device. The open portion of the device has surface 700, which is the user end of the handheld apparatus. The interior of the device houses all the components of the handheld device. The outer walls of the device are composed of a polymer or any light and sturdy material. The size of flat interface 700 accommodates for almost all areas of the human body. It is small enough to be placed on narrow or small surfaces of the body, such as the forearm, to scan those surfaces. Interface 700 is lined with light sources 704 and detectors 706 or panels thereof that emit light 708 and detect returning light 710. The flatness of the interface causes light waves to be emitted in a relatively uniform direction with fewer overlapping light waves than would if the surface were curved. The user may require manual operation to receive sufficient data to image the cutaneous layers and any areas of interest. For instance, the user may need to slowly move the handheld device across a patch of skin over a certain path to scan it completely. The distinctions between the embodiments employing optical fibers and electrical wires are disclosed immediately below.

Figure 8A:
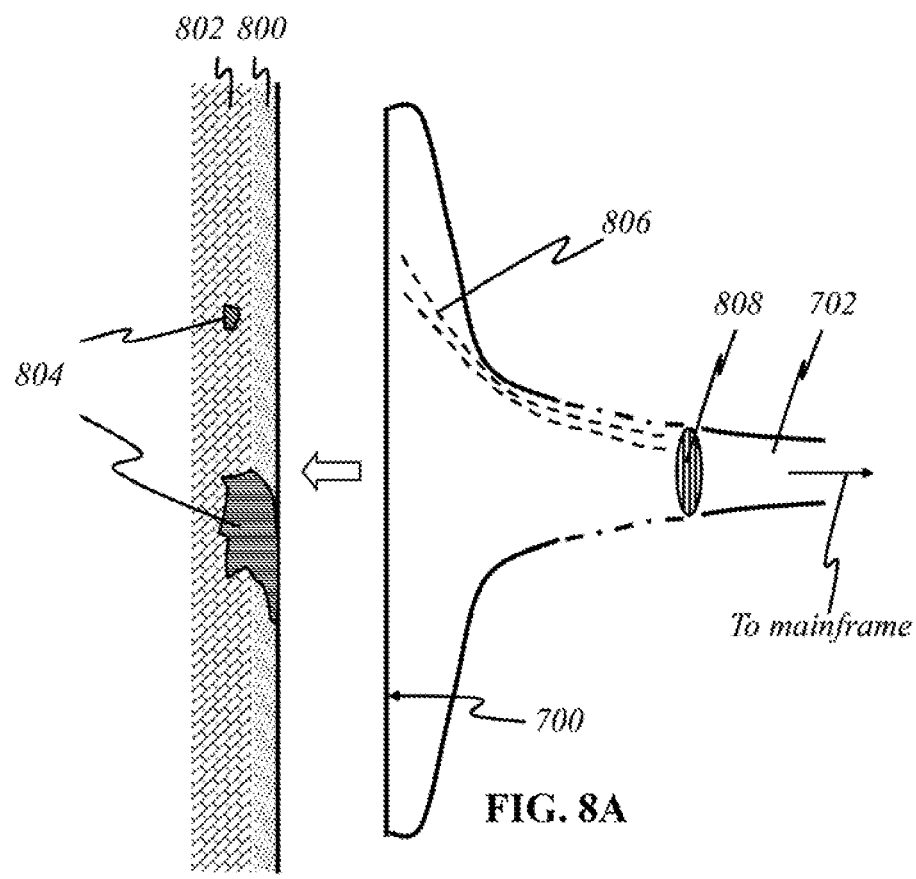
FIG. 8A shows a schematic of the preferred "flat" embodiment in a cross-sectional view.

FIG. 8A is a schematic showing a cross-sectional view of a preferred embodiment for a flat contact embodiment using optical fibers, taken along A-A' direction of FIG. 7, according to this invention. FIG. 8A illustrates a cross-section from FIG. 7 before skin makes contact with surface 700 of the device for imaging. The skin includes an epidermis 800, a dermis 802, and an area of interest 804. The flatness of interface 700 between skin and device is apparent from this perspective. The interior of the device contains individual 1:1 fiber or wire connections 806 between a light source or detector and a lens 808 and/or cable 702.

Each source and detector is connected to a cable. Source- and detector-to-cable fibers 806, 810 may be optical or electrical in nature. A couple of optical fibers 806 are illustrated in FIG. 8A in dashed lines. Each optical fiber 806 carries light signals, and each electrical wire 810 carries electrical signals. Light that comes through an optical fiber is collected and may be focused by lens 808, after which the light signals continue to propagate through cable 702 to be processed by the mainframe (not shown here). In some embodiments, lens 808 is not needed to focus light; instead, the light to and from the mainframe directly travels through optical fibers 806, between each sensor or detector and the mainframe.

FIG. 8B is a schematic showing the same cross-sectional view of a flexible contact embodiment but using electrical wires. The main difference from FIG. 8A is that a socket 810 and a connector 812 for a detachable electric cable 814 are used to separate the user end from the mainframe, which improves the capability of the device and cable 814 to be transported without loose extensions and stored in small spaces. Connector 812 allows attachment to socket 810.

In the flat contact embodiment illustrated in FIG. 8B, data are carried by electrical signals. As in the embodiment using optical fibers, surface 700 of the device is lined with numerous light sources and detectors or panels thereof that emit and detect light from the same direction, enabling the device to collect enough data to image epidermis 800, dermis 802, and any areas of interest 804. Having electrical cable 814 and detaching the device into separate components is possible and useful for compact storage. Electric cable 814 is preferably a ribbon cable, whose flat and flexible characteristics make it compact and simple to store or transport. In this embodiment, there is no lens that focuses light carried by optical fibers. Data are carried by electrical wires 810 that are lined and housed within the device. In some embodiments, the device can be connected to the mainframe by inserting connector 812 of electric ribbon cable 814 into socket 810 present on the outer shell of the device.

Electric pins 816 or other means of making contact with circuitry components may also be used. FIG. 8C is a schematic showing an enlarged view of the front of connector 812 of electric ribbon cable 814, which allows connection to socket 810 via electric pins 816 as a connection interface alternate to that of the ribbon cable. Socket 810 would have a shape that differs from that for a flat interface, according to the shape shown in FIG. 8B.

Figure 9A:
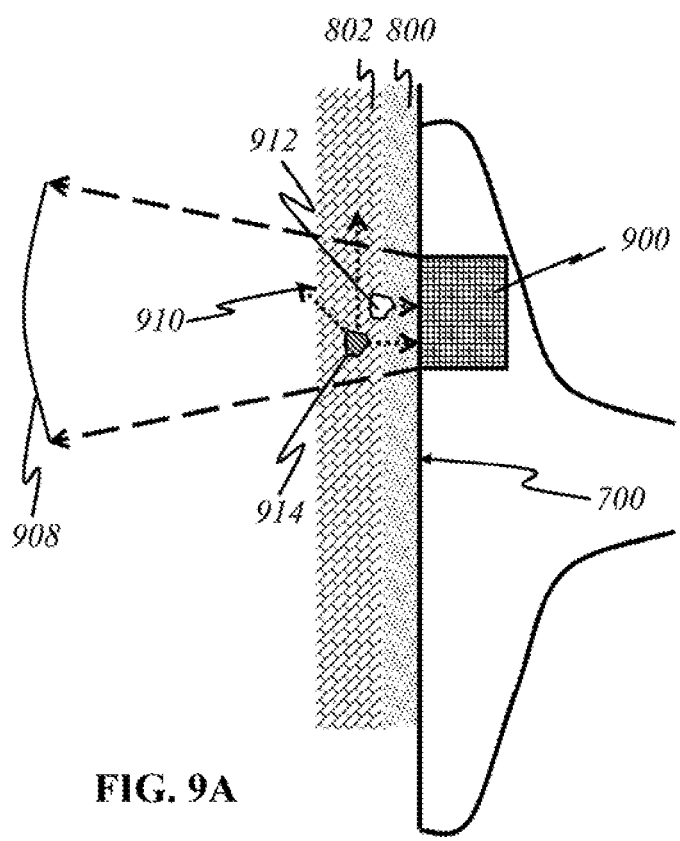
FIG. 9A shows a schematic of another preferred "flat" embodiment in a cross-sectional view.
Figure 9B:
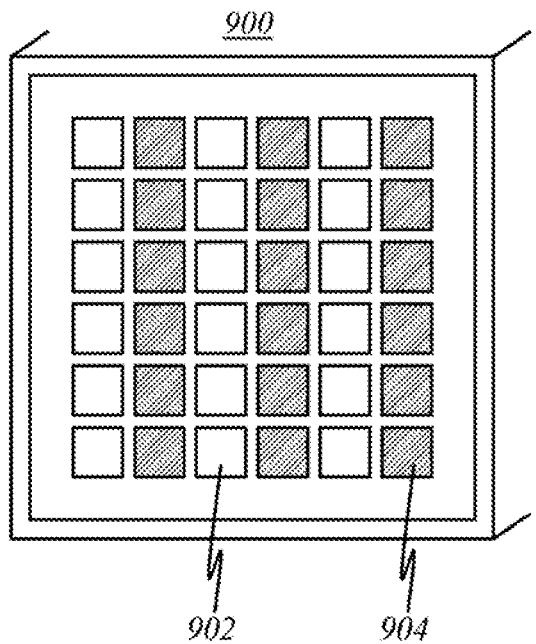
FIGS. 9B and 9C show schematics of a source-detector panel used in the preferred "flat" embodiment of FIG. 9A.
Figure 9C:
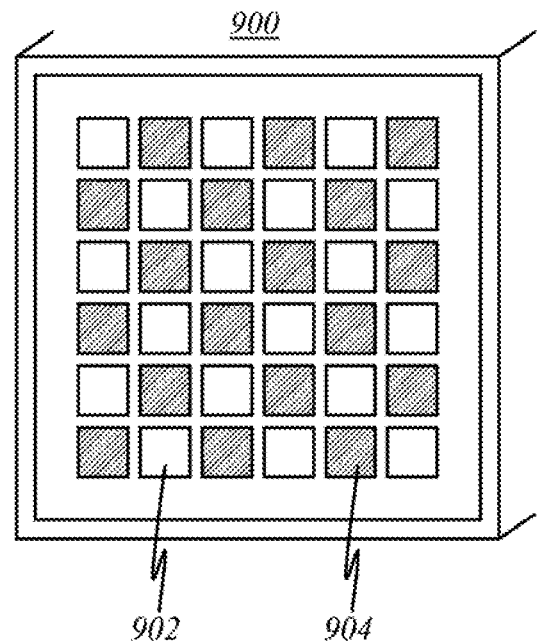

FIG. 9A is a schematic showing a cross-sectional view of a preferred embodiment for a flat contact embodiment of the user end of the device, taken along A-A' direction of FIG. 7 after the skin tissue makes contact with surface 700 for imaging, according to this invention, wherein like parts are indicated by like reference numerals as used previously, so that repeated explanation is omitted here. FIGS. 9A-9C apply to embodiments using either optical signals (FIG. 8A) or electrical signals (FIG. 8B). In FIG. 9A, the user has pressed the device onto a patch of skin comprising an epidermis 800 and a dermis 802 for examination. In a simplified representation, a panel 900 (out of at least one) containing both broadband sources and detectors is shown in this embodiment. Panel 900 is not to scale, but it would be possible to contain components as large as depicted on the interior side of surface 700 of the device that is in contact with the skin.

FIG. 9B illustrates a magnified view of the outward surface of panel 900. It is an illustrative 6×6 array of sources 902 and detectors 904 embedded, with each source 902 producing multispectral light 908 toward layers of skin 800, 802, each detector 904 receiving light 910 that has diffracted, reflected, or fluoresced. FIG. 9C illustrates a magnified view of another variation of the outward surface of panel 900. It is an illustrative 6×6 array of sources 902 and detectors 904 alternating in a checkerboard-like fashion, with each detector 904 receiving light 910, the light being emitted by sources 902. Numerous combinations of source 902 and detector 904 placement exist.

For purposes of illustration, panel 900 in FIG. 9A is emitting multispectral light 908 at arbitrary angles toward the patch of skin. Two arbitrary volumes of tissues are illustrated within epidermis 800 and dermis 802: one volume of normal tissue 912 and one volume of potentially malignant cells 914 (area of concern). Emitted light 908 is of a broadband spectrum, which carries a range of wavelengths relevant to the analysis of interested materials present 912, 914, taking into account the potential presence of precancerous or cancerous tissues and their possible depth distance from the surface of the skin. The outer surface of source-detector panel 900 is enlarged as shown in FIGS. 9B and 9C as 6×6 arrays of sources 902 and detectors 904 embedded in panel 900, with each source 902 producing multispectral light 908. Emitted light 908 travels into epidermal 800 and dermal 802 layers of the skin tissue and interacts with the components of the tissue. Depending on the size of potentially malignant tissue 914, light 908 hitting it will be diffracted or reflected. Assuming that tissue 914 is smaller than the wavelength of the emitted light, the light will scatter into multiple directions. One such light wave 910 is shown traveling back to the interface surface toward panel 900. In reality, light 910 will be scattered in numerous directions in a spherical shape. If detector 904 is able to detect the particular wavelength of the light wave, it then processes the signal for imaging or sends it to the mainframe (not shown here) for further processing and imaging. Based on known values of wavelengths that would be returned after reflecting or diffracting from skin cancer tumors, compared with known values of wavelengths that would be returned after reflecting off healthy skin tissue, the processor (not shown here) can determine the position and depth of the returning light to locate potential cancerous lesions. Three-dimensional images can be also produced from returning emissions, with which potential cancerous lesions can be viewed and interpreted on a display.

Figure 10A:
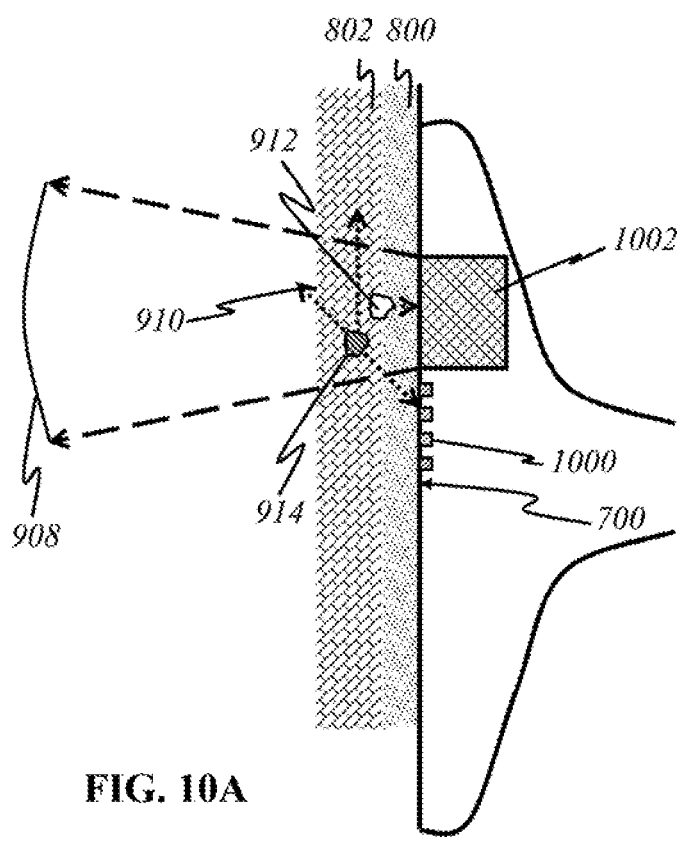
FIG. 10A shows a schematic of another preferred "flat" embodiment in a cross-sectional view.
Figure 10B:
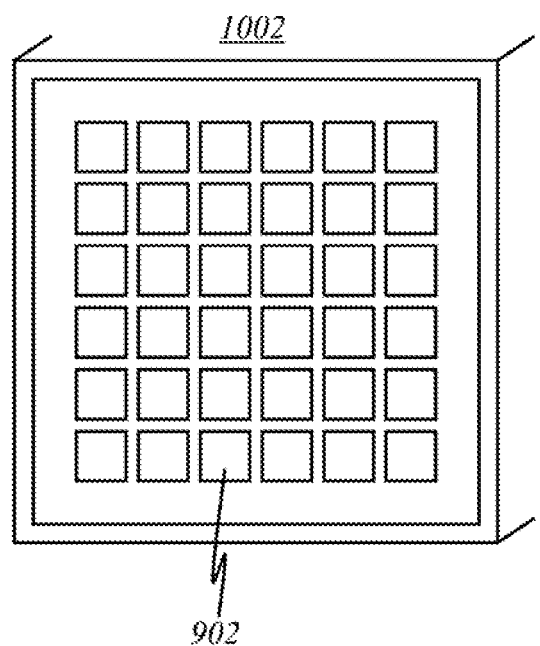
FIG. 10B shows a schematic of a source panel used in the preferred "flat" embodiment of FIG. 10A.

FIG. 10A illustrates a cross-sectional view of another preferred flat contact embodiment of the user end of the device. The main difference from FIG. 9A is that individual detectors 1000 are lined throughout interface surface 700, rather than grouped in a panel. Like parts are indicated by like reference numerals as used previously, so that repeated explanation is omitted here. In a simplified representation, a panel 1002 of broadband sources 904 is shown. A selected number of individual detectors 1000 (of numerous) are also shown. Multispectral light 908 travels from source panel 1002 to the skin. Assuming that potentially malignant tissue 914 is smaller than the wavelength of emitted light 910, the light will scatter into multiple directions. One such light wave 910 is shown traveling back to the interface surface toward detector 1000. If detector 1000 is able to detect the particular wavelength of light 910, it then processes the signal for imaging or sends it to the mainframe (not shown) for further processing and imaging. FIG. 10B illustrates a magnified view of the outward surface of source panel 1002. It is an illustrative 6×6 array of sources 902 embedded, with each source 902 producing multispectral light 908 toward layers of skin 800, 802.

Figure 11:
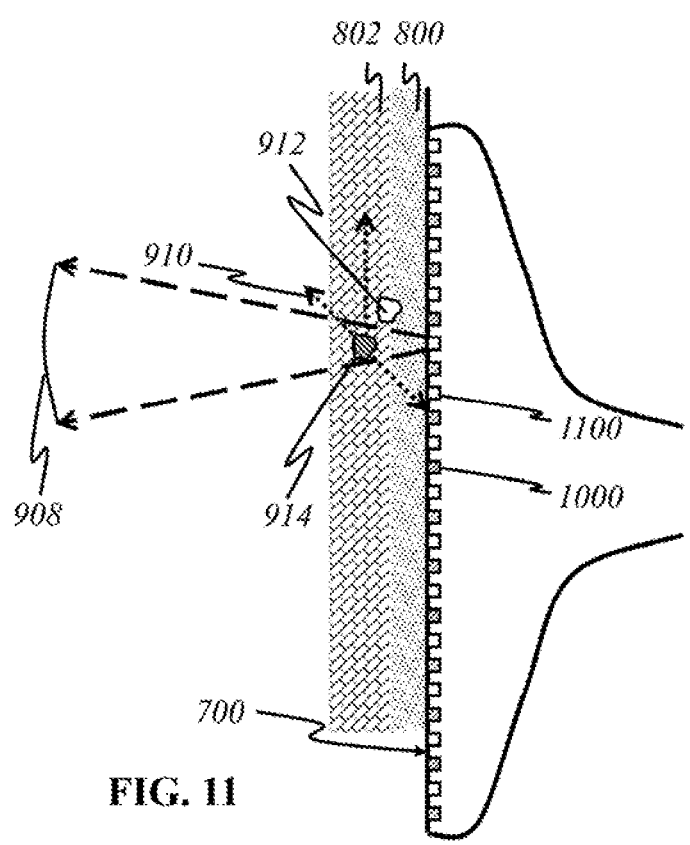
FIG. 11 shows a schematic of another preferred "flat" embodiment in a cross-sectional view.

FIG. 11 is a schematic showing a preferred embodiment according to this invention, wherein like parts are indicated by like reference numerals so that repeated explanation is omitted here. The main difference from FIGS. 9A and 10A is that both light sources 1100 and detectors 1000 are placed individually throughout inner surface 700, rather than grouped in a panel. From the aforementioned disclosures, other useful configurations will be apparent to those having ordinary skill in the art.

FIG. 12A shows a cross-sectional, top view of an alternate preferred non-contact embodiment of the device, which has pane 1200 suspended over a surface of a section of skin tissue 1204 ("non-contact embodiment"). Side panes 1202 may have soft support pad 1203 that allows the device to rest on patch of skin 1204 and maintain a constant distance with pane 1200. According to this invention, to make the device compact, the device comprises at least one foldable pane amenable to handheld use and transportation. Alternatively, the device can have more than one pane, wherein each pane 1200 holds light sources 1212 and detectors 1214, or panels thereof (see FIGS. 12B and 12C). In this embodiment, center pane 1200 holds light sources and detectors facing section of skin tissue 1204. Hinges 1206 allow side panes 1202 on the side to rotate along arcs 1208 and be held at desired angles relative to center pane 1200. There may be a handle 1210 or other means to grasp the device during operation.

FIG. 12B is a schematic showing a front view of the preferred embodiment for non-contact device according to this invention, wherein like parts are indicated by like reference numerals as shown in FIG. 12A, so that repeated explanation is omitted here. In FIG. 12B, side panes 1202 have been unfolded and are facing outward. Sources 1212 and detectors 1214 are individually placed on center pane 1200, although they may be grouped together in panels and may be broadband or uniband sources (see FIGS. 4-6). Alternatively, other variations of placement of sources 1212 and detectors 1214 are possible, for example, as illustrated in FIG. 12C. Here, the main difference from FIG. 12B is that sources 1212 and detectors 1214 are grouped in panels on center pane 1200.

During operation of the non-contact embodiment, the user places the device with pane 1200 and side panes 1202 opened on top of an area of skin with visible defect, such as the forearm with a colored spot—an area of interest. The user may require manual operation to receive sufficient data to image the epidermal and dermal layers of the skin along with any areas of interest. For instance, the user may need to slowly move the handheld device across the skin over sufficient amount of distance and area of the skin to scan it. Unlike other preferred embodiments previously disclosed in FIGS. 9, 10 and 11, there is no need to press the device into surface of skin 1204. In the embodiment illustrated in FIGS. 12A through 12C, while the device is in operation, broadband or uniband light sources 1212 from center pane 1200 emit light 1220 of varying wavelengths toward the object, i.e., skin, placed between side panes 1202. Reflected, diffracted, or fluoresced light 1222 travels back to a detector or panel thereof, on side panel 1202. If the detector is able to detect the particular wavelength of the light wave, it then processes the signal for imaging or sends it to the mainframe (not shown) via optical, electrical, or wireless connection for further processing and imaging. Based on known values of wavelengths that would be returned after reflecting or diffracting from skin cancer tumors rather than known values of wavelengths that would be returned after reflecting off healthy skin tissue, the processor can determine the position and depth of the returning light to locate potential cancerous lesions. Three-dimensional images are also produced from all returning light waves; thus, potentially cancerous lesions can be viewed and interpreted with human eyes.

One way to protect the user from overexposure to light is to place shields between the user's line of sight and light sources. FIG. 13A is a schematic showing a top view of the preferred embodiment for an alternate device, according to this invention, wherein like parts are indicated by like reference numerals so that related explanation is omitted here. The main difference from FIG. 12A is that shields 1300 are placed over panes 1200, 1202. Shields 1300 are deployed by unfolding them upward from panes 1200, 1202 along arcs 1302. They are composed of any material that will not be penetrated by the light wavelengths that are used by the device. Such a material should absorb rather than reflect. Alternatively, shields 1300 can be made from materials that can prevent light from partially or wholly escaping outside, such as a polymer, plastic, nano-composite fiber, carbon fiber, etc. Similar to panes 1200, 1202, shields 1300 can be adjusted and held at desired angles. In the illustration, engaged shields 1300 are locked into a substantially perpendicular angle with respect to panes 1200, 1202. The enclosure created by panes 1200, 1202 and shields 1300 minimizes the leakage of light 1220, 1222 from light sources 1212. In turn, the user is less likely to be irritated by light that she may see or wavelengths that may be harmful to the eyes during operation. The shield can be made from the material the type of which can be selected from the group consisting of polymer, plastic, nano-composite having the capability of absorbing the light having wavelengths to be absorbed. Alternatively, the shield can be made from the material which could be reflective for the light wavelengths of interest. In this case, the secondary reflective light from the shield are made to incident onto the detector(s) array (not shown here) for further processing the signal. The signal can be synchronized or asynchronized with the main detector panel described earlier. In this case, the shields can be designed in such a way that incoming lights and outgoing light (reflective) can be same direction or different direction (not shown here).

FIG. 13B is a schematic showing the device with front shield 1300, as shown in FIG. 12A, according to this invention, wherein like parts are indicated by like reference numerals so that related explanation is omitted here. In FIG. 13B, side panes 1202 have been unfolded and are facing outward. Sources 1212 and detectors 1214 are individually placed on center pane 1200, although they may be grouped together in panels 1304 and may be broadband or uniband sources as shown in FIGS. 4 to 6). Shields 1300 prevent light emitted by the sources from reaching the user's line of sight which remains above shields 1300 during normal operation. FIG. 13C is a schematic showing the same embodiment. The main difference from FIG. 13B is that sources 1212 and detectors 1214 are grouped in panels on center pane 1200. From the aforementioned disclosures, other useful configurations will be apparent to those having ordinary skill in the art.

FIG. 14 illustrates a cross-sectional view of an embodiment of the user end of the device that has an elongated, hollow extension 1400 that makes direct contact with the skin and has a panel 1401 of sources and detectors that does not make direct contact with the skin ("semi-contact embodiment"). In particular to temperature regulation, when the surface of the body is cold, blood vessels at the surface of the skin contract and force the blood deeper into the body, preventing heat loss by convective heat transfer. Contrarily, when the body feels too warm, it dissipates heat by expanding blood vessels to bring more blood to the surface of the skin. Redness may be caused by increased amount of saturated hemoglobin, an increase in the diameter or actual number of capillaries, or a combination of these factors. Given the increased level of heat dissipation and metabolic activity of the melanoma lesion, it is contemplated that this physiologic flushing caused by thermal exposure is characterized by a heat diffusion rate that differs between healthy skin and cancerous skin. Specifically, the rate of reaching normal body temperature (36.5 C) is more rapid in cancerous cells. After applying a heating stress by, for example, a stream of hot air onto an area of skin, any cancerous lesions present will return to steady-state temperature more quickly than healthy tissue, the differential being capable of measurement by the present invention.

This embodiment is intended to be used on an area of the skin that is suspected to harbor a cancerous lesion 1402 (area of interest). For example, a user may find a discolored area of the skin that seems different from other moles. User end 1400 of the device, having a mechanism 1403 for suction, is pressed over a patch of skin 1406, creating a temporarily sealed chamber enclosed by device 1400 and skin 1406. Alternatively, the chamber may be unsealed, e.g., with openings along the side or circumference of hollow extension 1400, to allow ventilation. A layer of thin material 1404 can further secure the location of the interface between skin and device. Orifices on the wall or walls of the device emit hot air 1408 that raises the temperature of skin 1406 to that of streams of air 1408. The air may be emitted with strong force or slowly to create an ambient temperature. In preferred embodiments, the temperature of the air is at most 50 C to prevent excessive discomfort from the heat. Certainly, the environment, global location, and pain threshold of the user will vary the discomfort level, and the temperature may reach higher than or lower than 50 C. The temperatures of the area of the skin affected is imaged using emitted light 1410 and returning light 1412, under a similar process as described above, and quantified during the period of time in which the affected areas cool down to steady-state body temperature. The location and the type of lesion (cancerous or healthy) can thus be detected, as there is no difference in the rate of reaching steady-state temperature between benign and healthy skin. Detecting a localized area that reaches steady state faster than the surrounding area may indicate that the localized area is cancerous and not healthy skin. In addition, water content in malignant melanoma is lower. Multispectral imaging provides insight by detecting the amount of hemoglobin, the amount of water, and temperature differentials across the skin's surface.

FIG. 15 illustrates the effect of applying a heating stress 1500 on an area of the skin 1502 at different times using a preferred embodiment of the present invention. Before application of heating stress 1500, the area of skin 1504 near the device (represented by the dashed circle) is generally the same temperature, approximately the normal body temperature of 36.5 C. After applying heating stress 1500 until the area of affected skin 1506 is raised, the same temperature as applied heat 1500, e.g., a stream of hot air, affected area 1506 is periodically imaged by the light sources and detectors from the device. If a cancerous lesion 1508 is not present in affected area 1506, the cooling rate of both affected area 1506 is uniform; there is no significant differential across affected area 1506. If cancerous lesion 1508 is present on affected area 1506, area having lesion 1508 reaches steady-state temperature and cools faster than the rest of affected area 1506. The difference in temperatures becomes marked over time. Wavelength data is periodically collected from the returning light to calculate the temperatures across the entirety of affected area 1506. For example, the image on the upper right of the figure shows the relative temperatures of patch of skin 1502 some time after the heating stress. One spot 1508, having an unconfirmed lesion, may have an average (across the surface) temperature of 40

C at this time; surrounding area 1506 may have a higher average temperature of 43 C at this time. The spot that is 40 C is likely to be a cancerous lesion because it is of a lower temperature than the surrounding tissue. Three-dimensional images may also be generated from the returning radiation. Three-dimensional analysis provides further confirmation as well as insight into how deeply a potentially cancerous lesion has progressed. Affected area 1506 of the skin eventually returns to the steady-state body temperature of 36.5 C.

FIG. 16 is a schematic showing a close-up view of an optical-fiber cable 1600, which comprises a bundle of optical fibers 1602. Numerous optical fibers 1602 are packed into cable 1600. Optical fibers 1602 are transparent and highly flexible fibers that are typically at most 0.5 mm. They can function as a waveguide for light 1604 traversing through. Containment of light 1604 is enabled by total internal reflection, which completely reflects light propagating along fiber 1602 hits the boundary of fiber 1602 at a critical angle, ideally close to parallel with the walls of fiber 1602. To confine and propagate light 1604 within fiber 1602, the light that enters cable 1600 must be within a certain range of angles, which a lens (see FIG. 8A) assists with.

Operational accuracy of the device can be improved by using a supplementary layer between the surface of the skin and the device. Refractive index n plays a role in characterizing biological tissues' response to optical illumination. The layer acts as an intermediary between two media of dissimilar refractive indices. For example, there is a disproportionate disparity between air and tissue if approximately n of air is 1.00, n of epidermis is 1.41, n of dermis is 1.36, and n of fatty tissue is 1.45. A medium with sufficiently disparate refractive index will tend to reflect light incident on that medium. The supplementary layer serves to introduce an intermediate n that mediates and bridges the gap between the disparate values between air and tissue, i.e., approximately between 1.00 and refractive indices of tissue components. Since the light incident must penetrate, the layer is transparent to light wavelengths of interest and reduces reflection. The layer is thin relative to the tissue, non-hazardous to the skin, and is easily removed or washed. The layer helps smooth out the target surface area of the skin, reducing variability and standardizing the experience among users of the device, because there may be different skin types, amount of hair present, and smoothness. Flattening the skin above the area the device operates on can reduce interference from microscopic obstacles and gaps present on the surface of the skin. The supplementary layer may be embodied and used in various ways as disclosed below.

Figure 17A:
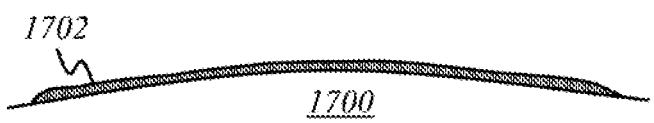
FIGS. 17A-17E show schematics of various forms of a supplementary layer used to improve functionalities of the present invention.

FIG. 17A illustrates a cross-sectional view of a section of skin 1700 and a gel layer 1702. A thin layer of gel 1702 is applied on the surface of section of skin 1700 over which the device will be placed. The thickness of the layer of gel 1702 is exaggerated to show the amorphous nature of gel 1702. It is easily washed from the skin as well as the device if the device has touched the gel. FIG. 171 is a highly enlarged cross-sectional view of the same section of skin 1700 as FIG. 17A. The main difference from FIG. 17A is that nanoparticles 1704 are embedded in gel 1702, which may be composed of ZnO, TiO2, and/or other metal oxide particles. Nanoparticles 1704 enable reduction or complete alleviation of the reflection of light, which enhances the clarity of images produced later.

Figure 17B:
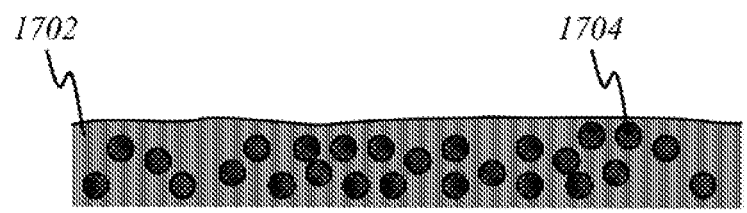
Figure 17C:
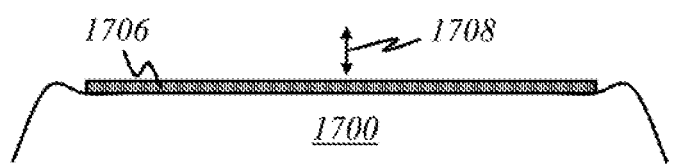

FIG. 17C illustrates a cross-sectional view of skin 1700 and a rigid layer 1706 pressing down on it. As with other forms of the supplementary layer, rigid layer 1706 is transparent to wavelengths of interest and is non-toxic to the skin. By applying force 1708 during application of rigid layer 1706, it flattens skin 1700 and smoothes out the surface of skin 1700. This serves two purposes: Reduce the reflection of light and the delta of refractive indices between air and components of skin 1700, and reduce variability of experience among different users. Rigid layer 1706 may be constructed inexpensively to be disposable.

Figure 17D:
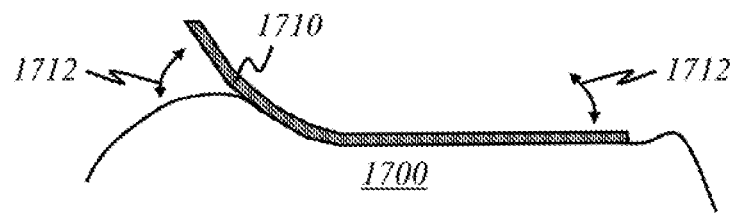
Figure 17E:
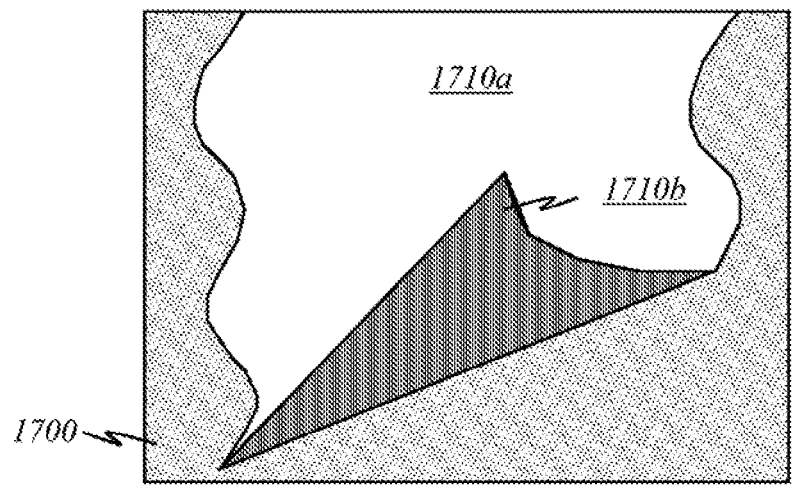

FIG. 17D illustrates a cross-sectional view of skin 1700 and one side of a flexible layer 1710 pressing down on it. As with other forms of the supplementary layer, flexible layer 1710 is transparent to wavelengths of interest and is non-toxic to the skin. Flexible layer 1710 may be extremely thin and malleable so as to be wrapped or stretched over the target area of skin. Similar to the rigid or gel embodiments as shown in FIGS. 17A-17C, flexible layer 1710 is serves to reduce the gap between disparate n values when light enters a different medium. By applying force 1712 toward or away during application of flexible layer 1710, the user has greater control over application of flexible layer 1710 as well as determination of which area of skin to apply it to. Flexible layer 1710 may be constructed inexpensively to be disposable. FIG. 173 is a schematic showing a top view of skin 1700 and a flexible layer 1710 as an alternative view of FIG. 17D. Top side 1710a of flexible layer 1710 is shown, and bottom side 1710b is shown being lifted from skin 1700. Flexible layer 1710 is malleable enough to be folded and partially bent upward as illustrated.

FIG. 18 is a schematic showing a whole view of implementations of operational parts of the preferred embodiment, according to this invention. A user end 1800 is the handheld portion for the user to aim and receive light. In embodiments using optical fibers to transfer light signals, light 1802 may be generated by sources placed in a mainframe 1804 rather than user end 1800. Likewise, detectors may be placed in mainframe 1804 rather than user end 1800. In other embodiments, sources and detectors may be placed on user end 1800, with a generic connection 1806a transferring data between the user end and the mainframe. Instructions or data 1808 containing instructions to emit light 1802 may travel from mainframe 1804 to user end 1800. Data 1810 on received light 1812 may travel from user end 1800 to mainframe 1804. Mainframe 1804 may include a processor 1814 and also other components, such as light sources, detectors, display screen, source driver, controller, signal amplifier, and digitizer (see FIG. 2). Different means of transferring data are possible. In some embodiments, connection 1806a between mainframe 1804 and user end 1800 is comprised of a bundle of optical fibers that transfer light. In some other embodiments, the connection is comprised of electrical wires, preferably a ribbon cable because it is highly compact and flexible. In yet other embodiments, the connection is wireless and lacks a physical connection.

In some embodiments, a display screen 1818 displays diagnosis results, images, and other information 1816 the user may be interested in. Display screen 1818 may be part of mainframe 1504, exist remotely on another apparatus dedicated to the device, or be on the user's separate electronic device, such as a mobile phone or a personal computer. User end 1800 communicates with mainframe 1804 to exchange data and instructions 1808, 1810. Various embodiments have different combinations wherein components are placed in different places, as described below.

FIG. 19 is a schematic of a whole view of an embodiment, according to this invention, wherein connection 1806b between user end 1800 and mainframe 1804 is of electrical nature. Like parts are indicated by like reference numerals as used previously, so that repeated explanation is omitted here.

The means of connection transfer only electrical signals. It delivers instructions 1808 from processor 1814 within mainframe 1804, enabling particular sources on user end 1800 to emit light 1802 at predetermined, particular wavelengths and/or predetermined, particular times as instructed. The detectors on user end 1800 register various reflected or diffracted light waves 1812. Data collected 1810 is transferred back to mainframe 1804, where useful data, such as sizes of areas of interest, depths of areas of interest, and images of the interior of the user's skin layers, are derived. Results derived 1816 can be displayed on screen 1818 for the user. Screen 1818 may be part of mainframe 1804, separate from mainframe 1804, or it could be on another device. For example, the screen may be on a mobile phone or a monitor of a personal computer may connect to mainframe 1804 and serve as the screen. Results 1816 may be sent to such a separate device, or it may be displayed on screen 1818 as part of mainframe 1804.

FIG. 20 is a schematic of a preferred embodiment, according to this invention, wherein like parts are indicated by like reference numerals as used previously, so that repeated explanation is omitted here. The main difference from FIG. 19 is that here, results 1816 are transferred to and displayed on a separate device or screen 1818 whereas all functions described in FIG. 19 are performed at the user end, i.e., user end 1800 contains the processor, sources, and detectors. Display screen 1818 is electrically connected to user end 1800.

FIG. 21 is a schematic diagram of a whole view of an embodiment, wherein the connection between user end 1800 and mainframe 1804 is of optical nature, able to transfer light. Like parts are indicated by like reference numerals as used previously, so that repeated explanation is omitted here. Here, instructions originate from user end 1800, and the sources operate to emit light 1802 at predetermined, particular wavelengths and/or predetermined, particular times. User end 1800 collects returning light waves 1812, which are directly transferred to mainframe 1804 via optical-fiber cable 1806c. Light received 1812 at the user end may be focused by a lens (not shown here) before being directly transferred through optical-fiber cable 1806c. Received optical signals 1812 are detected by detectors 1820, or a panel thereof, within mainframe 1804. Detected optical signals are processed to derive useful data 1816, such as confirming possible tumors, its size and location, and images of the interior of the user's skin layers. These data 1816 may be presented on display screen 1818. Screen 1818 may be part of mainframe 1804, separate from it, or it could be on another device. For example, the screen may be on a mobile phone or a monitor of a personal computer.

As a variation of this embodiment, in FIG. 22, optical-fiber cable 1806c transfers both emitted light 1802 and returning light 1812. Like parts are indicated by like reference numerals as used previously, so that repeated explanation is omitted here. The main difference from FIG. 21 is that in this embodiment, mainframe 1804 comprises both sources 1822 and detectors 1820. Using the unique properties of optical fibers, optical-fiber cable 1806c acts as a waveguide for light 1802, 1812 emitted from and returned to mainframe 1804, where the data is processed. In this embodiment, user end 1800 does not have any sources or detectors. It only acts as a mechanism to collect and focus light that is emitted and returned. As in the embodiment of FIG. 21, results 1816 may be sent to a separate device, or it may be displayed on screen 1818 as part of mainframe 1804.

FIG. 23 is a schematic of a preferred embodiment wherein the connection between user end 1800 and mainframe 1804 is wireless. Instructions 1808c to generate light 1802 and data 1810c on detected light 1812 are transmitted by wireless means. Instructions 1808c are generated from mainframe 1804, enabling particular sources on user end 1800 to emit light 1802 at predetermined, particular wavelengths and/or predetermined, particular times as instructed. The detectors on user end 1800 register various reflected or diffracted light waves 1812. Data 1810c collected is transferred wirelessly back to mainframe 1804, where useful data 1816, such as sizes of areas of interest, depths of areas of interest, and images of the interior of the user's skin layers, are derived. The results derived can be displayed on screen 1818 for the user. Screen 1818 may be part of mainframe 1804, separate from it, or it could be on another device. For example, the screen may be on a mobile phone or a monitor of a personal computer.

FIG. 24 is a schematic diagram of an embodiment in which all functions described in the previous FIG. 23 are performed at user end 1800, i.e., user end 1800 contains the processor, sources, and detectors. Like parts are indicated by like reference numerals as used previously, so that repeated explanation is omitted here. The main difference from FIG. 23 is that results 1816 are transferred, not from a separate mainframe but directly from user end 1800, to and displayed on a separate device or screen 1818. Display screen 1818 is connected to user end 1800 via wireless means.

Figure 25A:
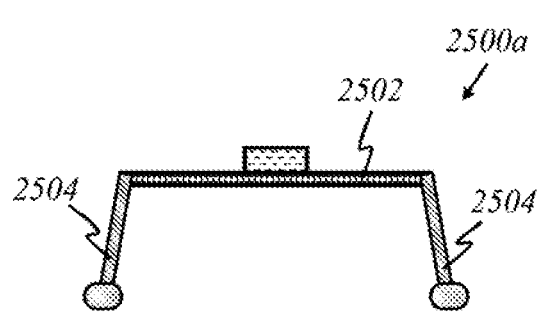
FIGS. 25A and 25B show schematics of the present invention implemented in various example devices.
Figure 25B:
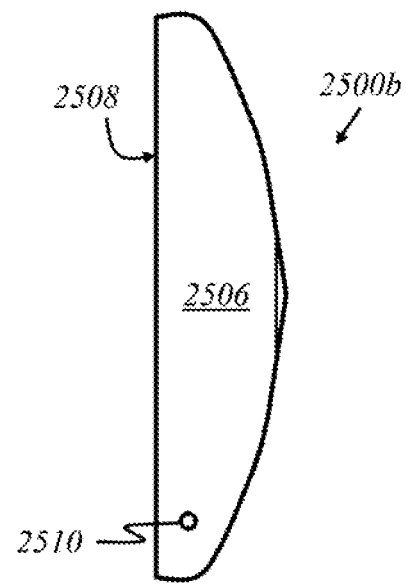

FIGS. 25A and 25B are schematic diagrams of various examples of shapes of devices and manufactures in which the functions disclosed thus far may be implemented. FIG. 25A shows an example of an embodiment of a device that implements the present invention. A top view of a flip-open non-contact type device 2500a having center pane 2502 and side panes 2504 is shown. As described in the text accompanying FIGS. 12 and 13, each pane 2502, 2504 has sources or detectors, or both, or panels thereof. The capability to adjust pane angles introduces compactness and flexibility in operating the device depending on the size and location of the patch of skin having area of concern. This type of device may implement at least the flip-open non-contact embodiments shown in FIGS. 12 and 13.

FIG. 25B shows another example of an embodiment of a device that implements the present invention and may implement at least the contact embodiments shown in FIGS. 7-11. A side view of a flat contact device 2500b having a user end 2506 is shown. An interfacing side 2508 of flat user end 2506 has a flat shape. Flat user end 2506 allows the user to press device 2500b to conform the skin to the shape of interfacing side 2508 of user end 2506. Direct contact enhances the quality of data acquired with a smaller margin of error. An example of a port 2510 is shown for connecting user end 2506 to other devices, such as a switch, control panel, display screen, computing device, and other peripheral devices, all of which may reside within user end 2506.

Also in the preferred embodiments, various ways are explained in a part of examples, but not for limitations, for detecting the targeted bio-mass, their types, and their location from the skin surface.

The present invention is expected to be found practically useful for detecting the early stage of cancers, particularly skin cancer. Furthermore, an apparatus is also described to transfer the data to the mobile device, or wirelessly sent to the electronic appliances. The apparatus can also be connected to the mobile device to achieve the image in the third device, outside of the apparatus, explained in the preferred embodiments.

Although, the invention has been described with respect to specific embodiment for complete and clear disclosure, the appended claims are not to be thus limited but are to be construed as embodying all modification and alternative constructions that may be occurred to one skilled in the art which fairly fall within the basic learning here is set forth.

The present invention is expected to be found practically use in the hand held based non-invasive cancer screening system where the broadband radiation is used to diagnosis initial stage of the cancer diagnosis, covering skin, breast etc. The application includes not only hand held type diagnosis system, but also combining with other detection system to increase the accuracy for the small to medium scale system.

Specific embodiments or examples, given in the detailed description of the present invention, are only used for clarifying the technical contents of the present invention, and are not narrowly interpreted in a limited manner to such specific examples, and various modifications may be made therein within the spirit of the present invention and the scope of the following claims.

What is claimed is:

1. A handheld imaging system comprising:
   an assembly comprising:
      a receptacle for directly contacting a biomass via a surface of the receptacle, the biomass comprising a target volume of tissue, wherein the biomass is substantially from one or more of an epidermal layer, a dermal layer, or a hypodermal layer;
      a light source configured to emit an incident coherent or broadband electromagnetic wave; and
      a light detector configured to detect a returning electromagnetic wave;
      wherein the light source and light detector convert between optical signals and electrical signals; and
      wherein the light source and the light detector are disposed along the surface of the receptacle; and
   a processor apparatus, which is optically or electrically connected to the light source and light detector, configured to cause the imaging system to:
      generate one or more optical signals, and cause the one or more optical signals to be emitted via the light source toward the biomass;
      based on an interaction of the emitted one or more optical signals with the target volume of tissue, cause production of one or more returning optical signals from the biomass;
      detect, via the light detector, the one or more returning optical signals;
      access data representative of at least (i) a plurality of spectral patterns associated with interaction of given optical signals with malignant dermal tissue, and (ii) a plurality of spectral patterns associated with interaction of the given optical signals with healthy dermal tissue;
      apply air to at least the biomass while the biomass is at a steady-state temperature and encased at least by the receptacle, the air having a temperature that is different than that of the biomass;
      during a period of time after the application of air and before the biomass has returned to the steady-state temperature, determine whether a first temperature associated with at least a first portion of the biomass is different from a second temperature associated with at least a second portion of the biomass; and
      based at least on (i) at least a portion of the accessed data and respective spectral patterns associated with the one or more returning optical signals, and (ii) a determination that, during the period of time, the second temperature associated with the at least second portion is lower than the first temperature associated with the at least first portion, determine that malignant dermal tissue is present in the at least second portion of the biomass, and determine one or more of a position or a depth of the malignant dermal tissue.

2. The handheld imaging system of claim 1, wherein the receptacle further comprises a side pane that can rotate around a hinge.

3. The handheld imaging system of claim 1, further comprising a cable that couples the receptacle to a computerized apparatus that is distinct from the assembly.

4. The handheld imaging system of claim 3, further comprising a lens that is configured to focus light.

5. The handheld imaging system of claim 1, wherein the light source is part of an array of light sources or a panel thereof, or an array of both light sources and light detectors or panels thereof.

6. The handheld imaging system of claim 1, wherein the light detector is part of an array of light detectors, an array of both light sources and light detectors, or a panel of light detectors.

7. The handheld imaging system of claim 1, wherein the receptacle, the light source, the light detector, and the processor apparatus are housed separately into a plurality of discrete devices.

8. The handheld imaging system of claim 7, wherein the plurality of discrete devices comprise a first device comprising the receptacle, the light source, and the light detector, and a second device comprising the processor apparatus.

9. The handheld imaging system of claim 8, wherein the first device and the second device are configured to perform data communication using at least one of an optical fiber, an electric cable, or a wireless interface.

10. The device of claim 1, further comprising an intermediary layer between the biomass and the receptacle, wherein a refractive index associated with the intermediary layer is between that of air and the biomass.

11. The handheld imaging system of claim 1, wherein at least a portion of the receptacle comprises a flat shape and is configured to make contact with the portion of the biomass.

12. The handheld imaging system of claim 1, wherein at least one side of the receptacle comprises a flat shape, and the light source and the light detector are disposed along an inner surface of the at least one side.

13. A method of screening for a malignant tumor in a tissue of a user, the method comprising:
   emitting one or more optical signals, via at least one light source, toward the tissue;
   detecting one or more returning optical signals, via at least one light detector, from the tissue;
   enabling access of data representative of a plurality of optical parameters associated with given optical signals that would return after interaction with malignant dermal tissue, the data being further representative of a plurality of optical parameters associated with the given optical signals that would return after interaction with non-malignant dermal tissue;
   causing application of a heating stress to the tissue so as to cause an increase in temperature to at least a portion of the tissue and surrounding portions thereof;
   detecting, based at least on the emitted one or more optical signals, whether a first rate of decrease of the temperature associated with the at least portion exceeds a second rate of decrease of the temperature associated with surrounding portions of the tissue; and based on (i) respective optical parameters associated with the detected one or more returning optical signals with at least a portion of the accessed data, and (ii) a detection that the first rate exceeds the second rate, causing determination of a malignancy of at least the portion of the tissue, the at least portion comprising the malignant tumor, and causing determination of one or more of a position or depth of the malignant tumor in the tissue.

14. The method of claim 13, further comprising enabling access of second data representative of a plurality of optical parameters associated with a given optical signal that would return after interaction with healthy dermal tissue;

wherein the determination of the correlation comprises determination of the correlation further based on an optical parameter associated with the detected one or more returning optical signals and the accessed second data.

15. The method of claim 13, further comprising causing production of an image based on at least the one or more returning optical signals, and causing a render of the image on a display.

16. The method of claim 13, wherein the tissue of the user makes direct contact with a surface of a handheld receptacle, the surface comprising both the at least one light source and the at least one light detector.

17. An apparatus for screening for a malignant tumor in dermal tissue, the apparatus comprising:

a processor apparatus;

an interface in data communication with the processor apparatus, the interface comprising a surface configured to directly contact the dermal tissue via one side of the surface, the interface further comprising at least one light source and at least one light detector disposed along another side of the surface; and a non-transitory computer-readable apparatus comprising a storage medium, the storage medium having a computer program comprising a plurality of instructions, the plurality of instructions being configured to, when executed by the processor apparatus, cause the apparatus to:

generate one or more optical signals, and cause the at least one light source to emit the one or more optical signals toward the dermal tissue;

receive one or more returning optical signals from the dermal tissue based on the emitted one or more optical signals;

access data representative of a plurality of optical parameters relating to interaction of given optical signals with the malignant tumor and a plurality of optical parameters relating to interaction of the given optical signals with healthy tissue;

cause application of air to the dermal tissue, the dermal tissue having a first temperature and the air having a second temperature; and based on (i) respective optical parameters corresponding to the one or more returning optical signals with at least a portion of the accessed data, and (ii) a temperature of a first portion of the dermal tissue being higher than a temperature of a second portion of the dermal tissue during a time subsequent to the application of air and prior to the dermal tissue reaching the first temperature, the temperatures of the first and second portions determined based on one or more second optical signals emitted toward the dermal tissue and received by the apparatus, determine a malignancy and a position of a volume of tissue within the dermal tissue, the volume of tissue corresponding to the second portion of the dermal tissue.

18. The apparatus of claim 17, wherein the plurality of optical parameters comprise a plurality of wavelengths associated with given returning optical signals that would be returned subsequent to reflection of the given optical signals from the malignant tumor.

19. The apparatus of claim 17, wherein the generated one or more optical signals comprises a plurality of wavelengths.

20. The apparatus of claim 17, wherein the determination of the malignancy comprises a determination that the volume of tissue comprises precancerous dermal tissue.

* * * * *